(12) United States Patent
Gladwin et al.

(10) Patent No.: US 9,114,109 B2
(45) Date of Patent: Aug. 25, 2015

(54) FIVE-COORDINATE NEUROGLOBIN AND USE THEREOF AS A BLOOD SUBSTITUTE

(75) Inventors: Mark T. Gladwin, Pittsburgh, PA (US); Daniel B. Kim-Shapiro, Winston-Salem, NC (US); Mauro Tiso, Bethesda, MD (US)

(73) Assignees: University of Pittsburgh—Of the Commonwealth System of Higher Education, Pittsburgh, PA (US); Wake Forest University, Winston-Salem, NC (US)

( * ) Notice: Subject to any disclaimer, the term of this patent is extended or adjusted under 35 U.S.C. 154(b) by 977 days.

(21) Appl. No.: 12/817,085

(22) Filed: Jun. 16, 2010

(65) Prior Publication Data

US 2010/0323029 A1 Dec. 23, 2010

Related U.S. Application Data

(60) Provisional application No. 61/187,527, filed on Jun. 16, 2009.

(51) Int. Cl.
*A61K 35/16* (2006.01)
*A61K 35/18* (2006.01)
*A61K 35/42* (2006.01)
*A61K 35/14* (2006.01)
*A61K 38/42* (2006.01)

(52) U.S. Cl.
CPC ............... *A61K 35/14* (2013.01); *A61K 35/16* (2013.01); *A61K 35/18* (2013.01); *A61K 38/42* (2013.01)

(58) Field of Classification Search
CPC ............................... A61K 35/14; A61K 38/42

USPC ........................................................ 435/183
See application file for complete search history.

(56) References Cited

U.S. PATENT DOCUMENTS

2003/0153491 A1* 8/2003 Winslow et al. ................... 514/6
2005/0069557 A1* 3/2005 Burmester et al. .......... 424/185.1

FOREIGN PATENT DOCUMENTS

WO   WO 2005/004884   1/2005
WO   WO 2009/298836   3/2009

OTHER PUBLICATIONS

Basu, et al., "Nitrite Reductase Activity of Cytochrome C," *J Biol Chem*, 283:32590-32597, 2008.

(Continued)

*Primary Examiner* — Sharmila G. Landau
*Assistant Examiner* — Sheridan Macauley
(74) *Attorney, Agent, or Firm* — Klarquist Sparkman, LLP

(57) ABSTRACT

Described herein is the finding that a mutant form of human neuroglobin (H64L) with a stable five-coordinate geometry reduces nitrite to nitric oxide approximately 2000-times faster than the wild type neuroglobin. Five-coordinate neuroglobin is also capable of binding and releasing oxygen. Based on these findings, the use of five-coordinate neuroglobin as a blood substitute is described herein. Particularly provided is a method of replacing blood and/or increasing oxygen delivery to tissues in a subject by administering to the subject a therapeutically effective amount of neuroglobin with a stable five-coordinate geometry. In some cases, five-coordinate neuroglobin is administered in combination with another therapeutic agent or composition, such as a second blood replacement product (for example, a hemoglobin-based oxygen carrier), a blood product (such as red blood cells, serum or plasma) or whole blood.

19 Claims, 17 Drawing Sheets

(56) References Cited

OTHER PUBLICATIONS

Brunori and Vallone, "Neuroglobin, Seven Years Later," *Cell Mol Life Sci*, 64:1259-1268, 2007.
Burmester and Hankeln, "What is the Function of Neuroglobin?," *J Exp Biol*, 212:1423-1428, 2009.
Burmester et al., "Neuroglobin and Cytoglobin: Genes, Proteins and Evolution," *IUBMB Life*, 56:703-707, 2004.
Burmester et al., "A Vertebrate Globin Expressed in the Brain," *Nature*, 407:520-523, 2000.
Bykova et al., "Identification of an Intermolecular Disulfide Bond in Barley Hemoglobin," *Biochem Biophys Res Commun*, 347:301-309, 2006.
Capece et al., "High Pressure Reveals Structural Determinants for Globin Hexacoordination: Neuroglobin and Myoglobin Cases," *Proteins*, 754:885-894, 2009.
Crawford et al., "Hypoxia, Red Blood Cells, and Nitrite Regulate NO-Dependent Hypoxic Vasodilation," *Blood*, 107:566-574, 2006.
Dewilde et al., "Biochemical Characterization and Ligand Binding Properties of Neuroglobin, a Novel Member of the Globin Family," *J Biol Chem*, 276:38949-38955, 2001.
Eisenach, "Hemoglobin-Based Oxygen Carriers," *Anesthesiology*, 111:946-963, 2009.
Fago et al., "The Reactions of Neuroglobin with CO: Evidence for Two Forms of the Ferrous Protein," *J Inorg Biochem*, 100:1339-1343, 2006.
Garrocho-Villegas et al., "Plant Hemoglobins: What We Know Six Decades After Their Discovery," *Gene*, 398:78-85, 2007.
Giuffrè et al., "Neuroglobin: Enzymatic Reduction and Oxygen Affinity," *Biochem Biophys Res Commun*, 367:893-898, 2008.
Greenberg et al., "Neuroglobin: An Endogenous Neuroprotectant," *Curr Opin Pharmacol*, 8:20-24, 2008.
Greenburg and Kim, "Hemoglobin-based Oxygen Carriers," *Crit Care*, 8Suppl 2:S61-S64, 2004.
Grubina et al., "Concerted Nitric Oxide Formation and Release from the Simultaneous Reactions of Nitrite with Deoxy- and Oxyhemoglobin," *J Biol Chem*, 282:12916-12927, 2007.
Grubina et al., "Nitrite Reductase Activity of Hemoglobin S (Sickle) Provides Insight into Contributions of Heme Redox Potential *Versus* Ligand Affinity," *J Biol Chem*, 2836:3628-3638, 2008.
Hamdane et al., "The Redox States of the Cell Regulates the Ligand Binding Affinity of Human Neuroglobin and Cytoglobin," *J Biol Chem*, 278:51713-51721, 2003.
Hamdane et al., "Coupling of the Heme and an Internal Disulfide Bond in Human Neuroglobin," *Micron*, 35:59-62, 2004.
Hankeln et al., "Neuroglobin and Cytoglobin in Search of their Role in the Vertebrate Globin Family," *J Inorg Biochem*, 99:110-119, 2005.
Hendgen-Cotta et al., "Nitrite Reductase Activity of Myoglobin Regulates Respiration and Cellular Viability in Myocardial Ischemia-Reperfusion Injury," *Proc Natl Acad Sci USA*, 105:10256-10261, 2008.
Huang et al., "Enzymatic Function of Hemoglobin as a Nitrite Reductase that Produces NO Under Allosteric Control," *J Clin Invest*, 115:2099-2107, 2005.
Khan et al., "Neuroglobin-Overexpressing Transgenic Mice are Resistant to Cerebral and Myocardial Ischemia," *Proc Natl Acad Sci USA*, 103:17944-17948, 2006.

Kiger et al., "Neuroglobin Ligand Binding Kinetics," *IUBMB Life*, 56:709-719, 2004.
Kriegl et al., "Ligand Binding and Protein Dynamics in Neuroglobin," *Proc Natl Acad Sci USA*, 99:7992-7997, 2002.
Liu et al., "Effects of Neuroglobin Over-Expression on Mitochondrial Function and Oxidative Stress Following Hypoxia/Reoxygenation in Cultured Neurons," *J Neurosci Res*, 87:164-170, 2009.
Nadra et al., "Exploring the Molecular Basis of Heme Coordination in Human Neuroglobin," *Proteins*, 71:695-705, 2008.
Nicolis et al., "Reactivity and Endogenous Modification by Nitrite and Hydrogen Peroxide: Does Human Neuroglobin Act Only as a Scavenger," *Biochem J*, 407:89-99, 2007.
Nienhaus et al., "Structural Dynamics in the Active Site of Murine Neuroglobin and Its Effects on Ligand Binding," *J Biol Chem*, 279(22):22944-22952, 2004.
Pesce et al., "Human Brain Neuroglobin Structure Reveals a Distinct Mode of Controlling Oxygen Affinity," *Structure*, 11:1087-1095, 2003.
Petersen et al., "Reactions of Ferrous Neuroglobin and Cytoglobin with Nitrite Under Anaerobic Conditions," *J Inorg Biochem*, 102:1777-1782, 2008.
Salhany, "Kinetics of Reaction of Nitrite with Deoxy Hemoglobin After Rapid Deoxygenation or Predeoxygenation by Dithionite Measured in Solution and Bound to the Cytoplasmic Domain of Band 3 (SLC4A1)," *Biochemistry*, 47:6059-6072, 2008.
Shiva et al., "Deoxymyoglobin Is a Nitrite Reductase That Generates Nitric Oxide and Regulates Mitochondrial Respiration," *Circ Res*, 100:654-661, 2007.
Silverman et al., "Hemoglobin-Based Oxygen Carriers," *Anesthesiology*, 111:946-963, 2009.
Smagghe et al., "Slow Ligand Binding Kinetics Dominate Ferrous Hexacoordinate Hemoglobin Reactivities and Reveal Differences Between Plants and Other Species," *Biochemistry*, 45:561-570, 2006.
Sun et al., "Neuroglobin is Up-Regulated by and Protects Neurons from Hypoxic-Ischemic Injury," *Proc Natl Acad Sci USA*, 98:15306-15311, 2001.
Te Lintel Hekkert et al., "Preoxygenated Hemoglobin-Based Oxygen Carrier HBOC-201 Annihilates Myocardial Ischemia During Brief Coronary Artery Occlusion in Pigs," *Am J Physiol Heart Circ Physiol*, 298:H1103-H1113, 2010.
Uzan et al., "Neuroglobin and Other Hexacoordinated Hemoglobins Show a Weak Temperature Dependence of Oxygen Binding," *Biophys J*, 87:1196-1204, 2004.
Wakasugi et al., "Oxidized Human Neuroglobin Acts as a Heterotrimeric Gα Protein Guanine Nucleotide Dissociation Inhibitor," *J Biol Chem*, 278:36505-36512, 2003.
Wang et al., "Effects of Neuroglobin Overexpression on Acute Brain Injury and Long-Term Outcomes After Focal Cerebral Ischemia," *Stroke*, 39:1869-1874, 2008.
Weiland et al., "Bis-Histidyl Hexacoordination in Hemoglobins Facilitates Heme Reduction Kinetics," *J Am Chem Soc*, 126:11930-11935, 2004.
Cosby et al., "Nitrite reduction to nitric oxide by deoxyhemoglobin vasodilates the human circulation," *Nat Med* 9(12):1498-1505, 2003.
Dejam et al., "Nitrite Infusion in Humans and Nonhuman Primates: Endocrine Effects, Pharmacokinetics, and Tolerance Formation," *Circulation* 116:1821-1831, 2007.

\* cited by examiner

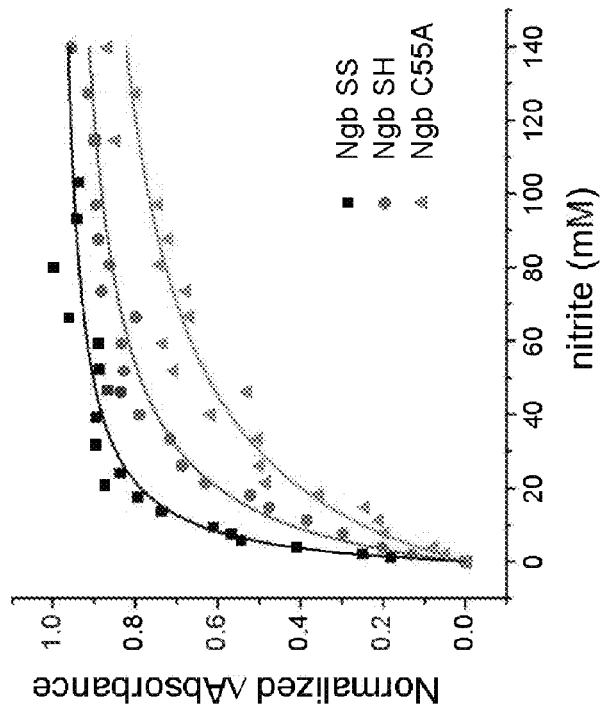
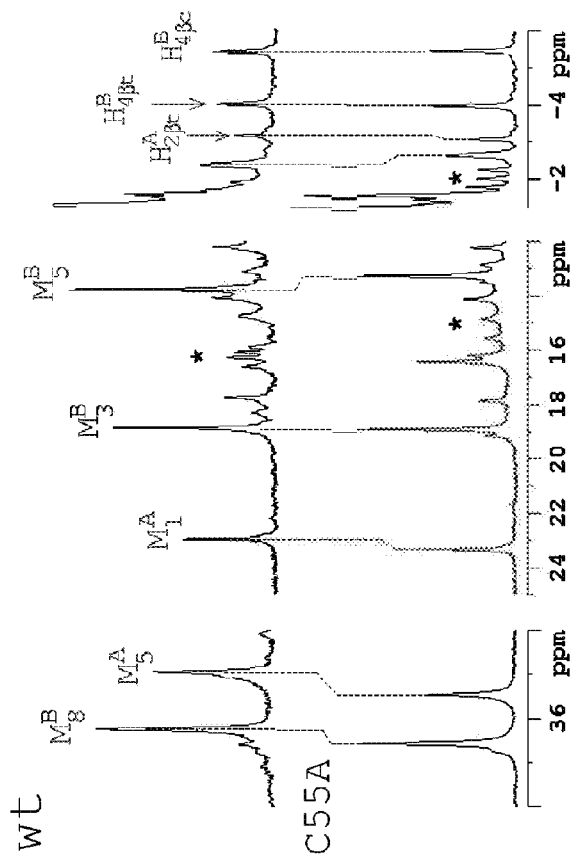
FIG. 2F
FIG. 2E

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 1
ctcttccagt acaacgcccg ccagttctcc ag                                       32

<210> SEQ ID NO 2
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 2
ctggagaact ggcgggcgtt gtactggaag ag                                       32

<210> SEQ ID NO 3
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 3
tccagcccag aggacgctct ctcctcgcct gag                                      33

<210> SEQ ID NO 4
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 4
ctcaggcgag gagagagcgt cctctgggct gga                                      33

<210> SEQ ID NO 5
<211> LENGTH: 33
<212> TYPE: DNA
<213> ORGANISM: Artificial Sequence
```

```
<220> FEATURE:
<223> OTHER INFORMATION: Synthetic oligonucleotide

<400> SEQUENCE: 5
ctgagttcct ggacctgatc aggaaggtga tgc                                    33

<210> SEQ ID NO 6
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 6
gcatcacctt cctgatcagg tccaggaact cag                                    33

<210> SEQ ID NO 7
<211> LENGTH: 1885
<212> TYPE: DNA
<213> ORGANISM: Homo sapiens
<220> FEATURE:
<221> NAME/KEY: CDS
<222> LOCATION: (376)..(831)

<400> SEQUENCE: 7
ttcccaggcc accatagcgg ctggcggagg gagcgcgcgc cttgctggcc tggagggggc        60 ggggccgtg gcggctttaa agcgcccagc ccaggcgtcg cggggtgggg cggctctggc       120
ggctgcgggg cgcagggcgc agcggccaag cggggtcccc ggaagcacag ctggggtgtc      180
tccacctacg actggccgcg cgccttttct ctcccgcgcc aggaaggag cggctgcggc       240 ccccgccggg cggaggcacg gggggcgtac gaggggcgga ggggaccgcg tcgcggagga      300
gatggcgcgg cacgtgcggt gacggcaccc gagcccgag ggtcccagcc ccgcgctccg       360
cgtccccggg acagc atg gag cgc ccg gag ccc gag ctg atc cgg cag agc      411
              Met Glu Arg Pro Glu Pro Glu Leu Ile Arg Gln Ser
                1               5                  10 tgg cgg gca gtg agc cgc agc ccg ctg gag cac ggc acc gtc ctg ttt       459
Trp Arg Ala Val Ser Arg Ser Pro Leu Glu His Gly Thr Val Leu Phe
         15                  20                  25 gcc agg ctg ttt gcc ctg gag cct gac ctg ctg ccc ctc ttc cag tac       507
Ala Arg Leu Phe Ala Leu Glu Pro Asp Leu Leu Pro Leu Phe Gln Tyr
     30                  35                  40 aac tgc cgc cag ttc tcc agc cca gag gac tgt ctc tcc tcg cct gag       555
Asn Cys Arg Gln Phe Ser Ser Pro Glu Asp Cys Leu Ser Ser Pro Glu
 45                  50                  55                  60 ttc ctg gac cac atc agg aag gtg atg ctc gtg att gat gct gca gtg       603
Phe Leu Asp His Ile Arg Lys Val Met Leu Val Ile Asp Ala Ala Val
                 65                  70                  75 acc aat gtg gaa gac ctg tcc tca ctg gag gag tac ctt gcc agc ctg       651
Thr Asn Val Glu Asp Leu Ser Ser Leu Glu Glu Tyr Leu Ala Ser Leu
             80                  85                  90 ggc agg aag cac cgg gca gtg ggt gtg aag ctc agc tcc ttc tcg aca       699
Gly Arg Lys His Arg Ala Val Gly Val Lys Leu Ser Ser Phe Ser Thr
         95                 100                 105 gtg ggt gag tct ctg ctc tac atg ctg gag aag tgt ctg ggc cct gcc       747
Val Gly Glu Ser Leu Leu Tyr Met Leu Glu Lys Cys Leu Gly Pro Ala
    110                 115                 120 ttc aca cca gcc aca cgg gct gcc tgg agc caa ctc tac ggg gcc gta       795
Phe Thr Pro Ala Thr Arg Ala Ala Trp Ser Gln Leu Tyr Gly Ala Val
125                 130                 135                 140 gtg cag gcc atg agt cga ggc tgg gat ggc gag taa gaggcgaccc            841
Val Gln Ala Met Ser Arg Gly Trp Asp Gly Glu
```

```
Val Gln Ala Met Ser Arg Gly Trp Asp Gly Glu
            145                 150 cgcccggcag cccccatcca tctgtgtctg tctgttggcc tgtatctgtt gtagcccagg    901
ctccccaagc ttccctgcat cttggtcctt gtccccttgg ccacactgga gaggtgatgg    961
ggcagggctg ggtctcagta tcctagagtc cagctgcaga aggagtggct tttcctccag   1021
gaagggcctt ctgggtgtcc cctcatcccc agtagcctct ttcttgcgtt tcttttacc    1081 ttttttggca ctccctctga ccccgcgatg agtgttttgg tggcagaggt gggatgagct   1141
ggaaaggtat ggaggtggga gaggatgggg ctcttctgtc tgtcctgctt cttcaggtga   1201
gtgcaggcca aggcggggt gagatggctg agcttccagc gccttctgtc ctgcctgccc    1261
agtcccttca ctgctttcct gccccaagat ggcttgcttt tcacaaataa agagaaagag   1321
cagctttagc cttcttggtg aatcccagg cagtgggagc agaatcagaa ctgccaggga    1381
agggaagggg gacctgggtc tcaatgggtc tcatttgagt ctcgcgggct gtgcagatgc   1441
cctgacagag tcggtttcct ttggcggcat tcccttttccc tcattcagca cttctgctgg  1501
gaactccctg actattccgc tgctgcagga acccagctag ctggccaggt ggggagggc    1561 tggggaccgg ccaggaagga ggggtgactt catcccagag agaccgagt tcccccagcc    1621 cttcatcacc aacccgctcc tgcaggagtg agtcttacct ccctggccc tcctttctgg   1681 ctcagcctgc agcgactgtg aggccacagc tcctcagatt cactgccgc tgtgtgccag   1741 tactcaggca gctggagaga agagaaggca gcagcagagg ccccgccct caccccagcc   1801 atctgcactt gtaccatttg ctctgtgctg actgtggtcc tataaattca tgagaaataa   1861
actggttctg tgtgcaaaaa aaaa                                          1885

<210> SEQ ID NO 8
<211> LENGTH: 151
<212> TYPE: PRT
<213> ORGANISM: Homo sapiens

<400> SEQUENCE: 8

Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
                20                  25                  30

Ala Leu Glu Pro Asp Leu Leu Pro Leu Phe Gln Tyr Asn Cys Arg Gln
            35                  40                  45

Phe Ser Ser Pro Glu Asp Cys Leu Ser Ser Pro Glu Phe Leu Asp His
        50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150

<210> SEQ ID NO 9
```

```
<211> LENGTH: 151
<212> TYPE: PRT
<213> ORGANISM: Artificial Sequence
<220> FEATURE:
<223> OTHER INFORMATION: Synthetic polypeptide

<400> SEQUENCE: 9

Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
            20                  25                  30

Ala Leu Glu Pro Asp Leu Leu Pro Leu Phe Gln Tyr Asn Cys Arg Gln
            35                  40                  45

Phe Ser Ser Pro Glu Asp Cys Leu Ser Ser Pro Glu Phe Leu Asp Leu
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150
```

FIVE-COORDINATE NEUROGLOBIN AND USE THEREOF AS A BLOOD SUBSTITUTE

CROSS REFERENCE TO RELATED APPLICATIONS

This application claims the benefit of U.S. Provisional Application No. 61/187,527, filed on Jun. 16, 2009, which is incorporated herein by reference in its entirety.

ACKNOWLEDGMENT OF GOVERNMENT SUPPORT

This invention was made with government support grant number HL058091 awarded by the National Institutes of Health. The government has certain rights in the invention.

FIELD

This disclosure concerns neuroglobin with a stable five-coordinate geometry and its use as a cell-free blood substitute.

BACKGROUND

A phylogenic analysis of the heme-globin family of proteins indicates that the well-characterized proteins hemoglobin and myoglobin were antedated by neuroglobin, which existed already 800 million years ago (Hankeln et al., *J Inorg Biochem* 99:110-119, 2005; Brunori and Vallone, *Cell Mol Life Sci* 64:1259-1268, 2007). Neuroglobin (Ngb) sequences remained highly conserved throughout mammalian evolution, suggesting a strongly selected vital functionality (Burmester et al., *IUBMB Life* 56:703-707, 2004). This heme containing, monomeric, 16.9 kDa protein shares 21-25% sequence homology with myoglobin and hemoglobin. However, unlike myoglobin and hemoglobin, it possesses a bis-histidine six-coordinate heme geometry, such that the proximal and distal histidines in the heme pocket are directly bonded to the heme iron (both $Fe^{+2}$ or $Fe^{+3}$ oxidation states) (Dewilde et al., *J Biol Chem* 276:38949-38955, 2001). Indeed, at equilibrium the concentration of the five-coordinate neuroglobin is very low, reported from 0.1 up to 5% (Uzan et al., *Biophys J* 87:1196-1204, 2004). Binding of oxygen or other gas ligands, such as nitric oxide (NO) or carbon monoxide, to the heme iron occurs upon displacement of the $6^{th}$ coordination bond with the distal histidine 64 residue (Capece et al., *Proteins* 75(4):885-894, 2009; Kriegl et al., *Proc Natl Acad Sci USA* 99:7992-7997, 2002). Despite this structural difference with myoglobin, neuroglobin displays comparable α-helix globin folding and high oxygen affinity ($P_{50}$ about 1-2 mmHg at 20° C.) (Kiger et al., *IUBMB Life* 56:709-719, 2004; Giuffre et al., *Biochem Biophys Res Commun* 367:893-898, 2008). However, the low tissue concentration of neuroglobin and the rapid auto-oxidation of the oxygen bound species suggest neuroglobin has not evolved to store and supply oxygen, leading to a number of different hypotheses about the physiological function of this conserved heme-globin (Brunori and Vallone, *Cell Mol Life Sci* 64:1259-1268, 2007; Burmester and Hankeln, *J Exp Biol* 212:1423-1428, 2009).

Despite uncertainty about the molecular functionality of neuroglobin, expression of this protein produces cytoprotective effects in vitro and in vivo, limiting neuronal cell death during glucose deprivation and hypoxia and limiting the volume of brain infarction in stroke models (Greenberg et al., *Curr Opin Pharmacol* 8:20-24, 2008; Khan et al., *Proc Natl Acad Sci USA* 103:17944-17948, 2006; Wang et al., *Stroke* 39:1869-1874, 2008; Sun et al., *Proc Natl Acad Sci USA* 98:15306-15311, 2001). An understanding of the functionality of neuroglobin could provide a paradigm shift in both biology and therapeutics, because many heme proteins in plants, bacteria, invertebrates and vertebrates are both highly conserved and exist in equilibrium between dominant six-coordinate geometry and the lower frequency five-coordinate state. Examples of these six-coordinate heme-proteins include cytoglobin, cytochrome c, *Drosophila melanogaster* hemoglobin, and the plant hemoglobins (Weiland et al., *J Am Chem Soc* 126:11930-11935, 2004; Nadra et al., *Proteins* 71:695-705, 2008; Garrocho-Villegas et al., *Gene* 398:78-85, 2007).

Over the last five years, groups have examined the ability of deoxygenated hemoglobin and myoglobin to react with and reduce nitrite to NO (Huang et al., *J Clin Invest* 115:2099-2107, 2005; Shiva et al., *Circ Res* 100:654-661, 2007). It has been proposed that this reaction serves a function similar to the bacterial nitrite reductases, in which a coupled electron and proton transfer to nitrite generates NO.

$$Fe^{+2}+NO_2^-+H^+ \rightarrow Fe^{+3}+NO.+OH^- \qquad \text{(equation 1)}$$

In the heart, myoglobin can reduce nitrite to NO to regulate hypoxic mitochondrial respiration and enhance the cellular resilience to prolonged ischemia, analogous to the cytoprotective effects of neuroglobin (Shiva et al., *Circ Res* 100:654-661, 2007). Studies using the myoglobin knockout mouse have now confirmed that myoglobin is necessary for nitrite-dependent NO and cGMP generation in the heart, nitrite-dependent cytoprotection after ischemia/reperfusion and nitrite-dependent control of hypoxic cellular respiration (Hendgen-Cotta et al., *Proc Natl Acad Sci USA* 105:10256-10261, 2008). It is therefore apparent that both myoglobin and neuroglobin may have roles in limiting cell death after ischemia-reperfusion injury. Of relevance to neuroglobin, it has recently been discovered that the mitochondrial protein cytochrome c can reduce nitrite to NO more rapidly than either hemoglobin or myoglobin, but only when it assumes the five-coordinate conformation (Basu et al., *J Biol Chem* 283:32590-32597, 2008). This conformation only occurs during the interaction with anionic phospholipids or upon oxidation or nitration of protein residues, suggesting a post-translational tertiary structure regulation of nitrite reduction and NO generation.

Interestingly, human neuroglobin contains two surface cysteines (C46 and C55) that form a disulfide bridge upon oxidation (Hamdane et al., *J Biol Chem* 278:51713-51721, 2003). Disulfide bond formation is accompanied by a decrease in the distal histidine binding affinity to heme iron ($K_{His}$, has been shown to decrease from ~3000 to 280, values calculated as $k_{on}/k_{off}$ are dimensionless) (Hamdane et al., *Micron* 35:59-62, 2004). This in turn increases the sub-population of five-coordinate neuroglobin and increases the affinity for endogenous ligands such as oxygen ($P_{50}$ shift from about 9 to 1 mmHg) (Hamdane et al., *J Biol Chem* 278:51713-51721, 2003). Nicolis et al. reported that the oxidized disulfide-bridged neuroglobin also exhibits a higher affinity for nitrite than the thiol reduced form (Nicolis et al., *Biochem J* 407:89-99, 2007).

SUMMARY

Disclosed herein is the surprising finding that stable five-coordinate neuroglobin is capable of very rapidly converting nitrite to NO. Five-coordinate neuroglobin is also capable of binding and releasing oxygen. Based on these important features, the use of five-coordinate neuroglobin as a blood substitute is provided herein. Many of the previously described blood substitutes are associated with cardiovascular complications due to NO scavenging, thus five-coordinate neuroglobin represents a therapeutic compound with the potential to alleviate the toxicity associated with previous blood substitutes.

Provided herein is a method of replacing blood and/or increasing oxygen delivery to tissues in a subject. In some embodiments, the method includes administering to the subject a therapeutically effective amount of neuroglobin with a stable five-coordinate geometry. The subject to be treated, for example, is any subject in need of increasing blood volume and/or increasing oxygen and/or NO delivery to tissues. In some embodiments, the subject has or is at risk of developing a disease, disorder or injury associated with a deficiency in red blood cells and/or hemoglobin, or associated with a reduction in oxygen delivery to tissues. In some embodiments, the subject to be treated suffers from or is at risk of suffering from a disease or condition associated with decreased blood flow, such as myocardial infarction, stroke, ischemia-reperfusion injury, pulmonary hypertension or vasospasm.

In some embodiments of the methods disclosed herein, stable five-coordinate neuroglobin is recombinant human neuroglobin. In particular examples, five-coordinate neuroglobin is H64L neuroglobin.

In some embodiments, the method further includes administering to the subject a second blood replacement product, a blood product or whole blood.

The foregoing and other objects, features, and advantages of the invention will become more apparent from the following detailed description, which proceeds with reference to the accompanying figures.

SEQUENCE LISTING

Figure 1B:
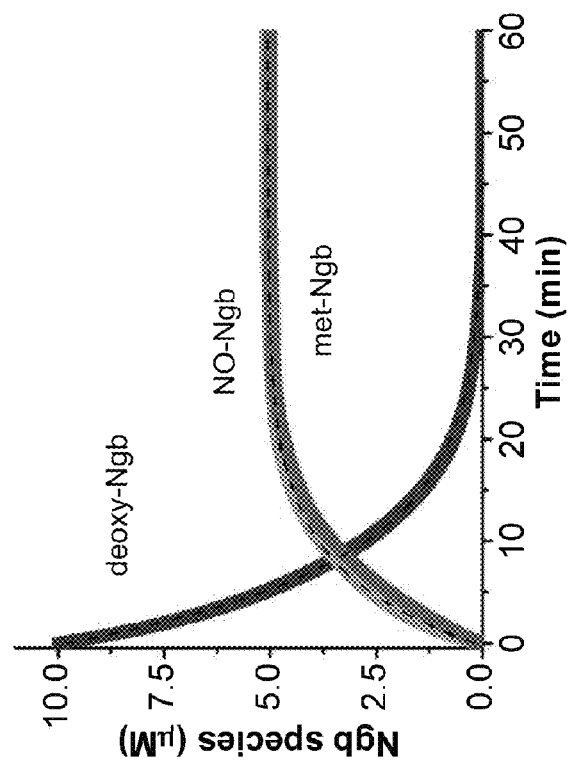
FIG. 1: Anaerobic reaction of deoxyneuroglobin with nitrite in the absence and in the presence of dithionite. (A) Selected visible spectra of the reaction between 10 μM deoxyNgb and 10 mM nitrite at 1 minute intervals. (B) Time-dependent changes of deoxyNgb, iron-nitrosyl-Ngb and total met-Ngb concentration during the reaction. (C) Selected visible spectra of the reaction between 10 μM deoxyNgb and 10 mM nitrite in the presence of 3 mM dithionite at 1 minute intervals. (D) Time-dependent changes of deoxyNgb, iron-nitrosyl-Ngb and total met-Ngb concentration during the reaction in the presence of 3 mM dithionite. (E) Plot of observed rate constants ($k_{obs}$) versus nitrite concentration; the second-order bimolecular rate constant obtained from the linear fit of the data is $0.12 \pm 0.02$ M$^{-1}$ sec$^{-1}$. (F) Effect of pH on the nitrite reductase reaction rates. Inset: BRC is linear with the proton concentration and it extends through the zero point (line shows linear regression analysis of the data). All measurements were made in 100 mM phosphate buffer and 25° C. as described in Example 1.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 16, 2010, 8.29 KB, which is incorporated by reference herein.

In the accompanying sequence listing:

SEQ ID NOs: 1-6 are the nucleotide sequences of oligonucleotides used for site-directed mutagenesis of neuroglobin.

SEQ ID NOs: 7 and 8 are the nucleotide and amino acid sequences of human neuroglobin (GenBank Accession No. NM_021257, incorporated herein by reference as it appears in the GenBank database on Jun. 16, 2010).

SEQ ID NO: 9 is the amino acid sequence of H64L neuroglobin.

DETAILED DESCRIPTION

I. Introduction

Hemoglobin and myoglobin evolved from a common ancestor of neuroglobin, a highly conserved hemoprotein of uncertain physiological function. Neuroglobin possesses a bis-histidine six-coordinate heme geometry, such that the proximal and distal histidines in the heme pocket are directly bound to the heme iron. The present disclosure describes the new finding that deoxygenated human neuroglobin reacts with and reduces nitrite to form NO. Remarkably, this reaction is allosterically regulated by redox sensitive surface thiols, cysteine 55 and 46, which regulate the open probability of heme pocket, nitrite binding and NO formation. Using site directed mutagenesis, it was demonstrated herein that a stable five-coordinate neuroglobin mutant (H64L) reduces nitrite to NO approximately 2000-times faster than wild type neuroglobin, while mutation of either C55 or C46 to alanine stabilizes the six-coordinate structure and slows the reaction. Lentivirus expression systems were used to confirm that the six-to-five coordinate status of neuroglobin regulates canonical intracellular hypoxic NO signaling pathways These studies suggest that neuroglobin functions as a post-translationally redox-regulated nitrite reductase that generates NO under six-to-five coordinate heme pocket control. The surprising ability of five-coordinate neuroglobin to rapidly convert nitrite to NO, and its ability to bind and release oxygen, makes five-coordinate neuroglobin a potential cell-free, hemoglobin-based blood substitute. As many of the previously described blood substitutes are associated with cardiovascular complications (e.g., vasoconstriction, brachycardia, and hypertension) due to NO scavenging, five coordinate neuroglobin represents a novel therapeutic compound with the potential to solve the major toxicity of current blood substitutes.

II. Abbreviations

BRC bimolecular rate constant
DTT dithiothreitol
EPR electron paramagnetic resonance
GSH reduced glutathione
GSSG oxidized glutathione
HBOC hemoglobin-based oxygen carrier
IPTG isopropyl-β-D-thio-galactosidase
Mb myoglobin
Met-Ngb ferric neuroglobin
Ngb neuroglobin
NMR nuclear magnetic resonance
NO nitric oxide
PFC perfluorocarbon
RBC red blood cell
SH reduced thiol
SS oxidized thiol
UV ultraviolet III. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Anemia: A deficiency of red blood cells and/or hemoglobin. Anemia is the most common disorder of the blood, and it results in a reduced ability of blood to transfer oxygen to the tissues. Since all human cells depend on oxygen for survival, varying degrees of anemia can have a wide range of clinical consequences. The three main classes of anemia include excessive blood loss (acutely such as a hemorrhage or chronically through low-volume loss), excessive blood cell destruction (hemolysis) or deficient red blood cell production (ineffective hematopoiesis).

The term "anemia" refers to all types of clinical anemia, including but not limited to: microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle-cell anemia, warm autoimmune hemolytic anemia, cold agglutinin hemolytic anemia.

In severe cases of anemia, or with ongoing blood loss, a blood transfusion may be necessary. Doctors may use any of a number of clinically accepted criteria to determine that a blood transfusion is necessary to treat a subject with anemia. For instance, the currently accepted Rivers protocol for early goal-directed therapy for sepsis requires keeping the hematocrit above 30.

Anoxia: A pathological condition in which the body as a whole or region of the body is completely deprived of oxygen supply.

Bleeding disorder: A general term for a wide range of medical problems that lead to poor blood clotting and continuous bleeding. Doctors also refer to bleeding disorders by terms such as, for example, coagulopathy, abnormal bleeding and clotting disorders. Bleeding disorders include any congenital, acquired or induced defect that results in abnormal (or pathological) bleeding. Examples include, but are not limited to, disorders of insufficient clotting or hemostasis, such as hemophilia A (a deficiency in Factor VIII), hemophilia B (a deficiency in Factor IX), hemophilia C (a deficiency in Factor XI), other clotting factor deficiencies (such as Factor VII or Factor XIII), abnormal levels of clotting factor inhibitors, platelet disorders, thrombocytopenia, vitamin K deficiency and von Willebrand's disease.

Bleeding episode: Refers to an occurrence of uncontrolled, excessive and/or pathological bleeding. Bleeding episodes can result from, for example, drug-induced bleeding (such as bleeding induced by non-steroidal anti-inflammatory drugs or warfarin), anticoagulant overdose or poisoning, aneurysm, blood vessel rupture, surgery and traumatic injury (including, for example, abrasions, contusions, lacerations, incisions or gunshot wounds). Bleeding episodes can also result from diseases such as cancer, gastrointestinal ulceration or from infection.

Blood: The fluid that circulates through the heart, arteries, capillaries and veins (that is, the circulatory system), and is the primary transport mechanism in the body. Blood transports oxygen from the lungs to the body tissues and carbon dioxide from the tissues to the lungs. Blood also transports nutritive substances and metabolites to the tissues and removes waste products to the kidneys and other organs for excretion. In addition, blood plays a critical role in maintenance of fluid balance. Blood has two primary parts—plasma (the fluid portion) and formed elements (the solid components). The solid components of blood include erythrocytes (red blood cells), leukocytes (white blood cells) and platelets. As used herein, "whole blood" refers to blood that has not had any components removed (blood that contains both the fluid and solid components). A "blood product" refers to one or more components of the blood, such as red blood cells, serum or plasma.

Blood replacement product or blood substitute: A composition used to fill fluid volume and/or carry oxygen and other blood gases in the cardiovascular system. Blood substitutes include, for example, volume expanders (to increase blood volume) and oxygen therapeutics (to transport oxygen in blood). Oxygen therapeutics include, for example, hemoglobin-based oxygen carriers (HBOC) and perfluorocarbons (PFCs).

An excellent blood substitute is one which mimics the oxygen-carrying capacity of hemoglobin, which requires no cross-matching or compatibility testing, with a long shelf life, which exhibits a long intravascular half life (over days and weeks), and which is free of side effects and pathogens.

The general task of blood within the frame of classic transfusion medicine is to supply oxygen to tissue (oxygen transport from lung to tissue, oxygen release and picking up carbon dioxide). All of this is accomplished by hemoglobin (Hb), the oxygen carrier protein contained within red cells. Early attempts to develop blood substitutes were focused on simple cell-free solutions of hemoglobin. Studies conducted in animal systems showed that infusion of cell-free hemoglobin caused a substantial increase in oncotic pressure because of its hyperosmolarity, coagulopathy, and hypertensive properties.

One significant problem and source of free hemoglobin's hypertensive properties was the affinity of Hb for nitric oxide (NO). NO produced by endothelial cells affects smooth muscle cells of the vessel wall and modulates the vascular tone toward vasodilatation. Cell-free Hb scavenges NO and shifts vasomotor tone toward vasoconstriction. Cell-free hemoglobin-induced vasoconstriction leads to serious side effects during transfusion of a subject manifested as an increase in systemic and pulmonary artery pressure without normalizing cardiac output or restoring intravascular volume. Decreases in the cardiac index impair optimum oxygen delivery and outweigh the advantage of an oxygen-carrying solution. Severe vasoconstriction complications caused the termination of clinical trials of unmodified cell-free hemoglobin as a blood substitute.

Modified Hb molecules have been produced in an attempt to overcome other limitations of Hb for use in a blood substitute, for example the penetration of Hb molecules into the interstitial space of the subendothelial layers of blood vessel walls and the sensitization of peripheral $\alpha$-adrenergic receptors. Successful modifications include purification, cross-linkage, and polymerization. Administration of these modified hemoglobins leads to vasoconstrictive effects that may increase systemic and pulmonary vascular resistance with resultant decreases in cardiac index. Clinical trials with these modified hemoglobins in healthy volunteers showed dose-dependent moderate or severe abdominal pain and increases in mean arterial pressure. The current state of the art is that there are no cell-free blood substitutes approved for clinical use for humans in the United States.

Burns: Any extremity experienced by the skin caused by heat, cold, electricity, chemicals, friction or radiation.

Cell-free or Stroma-free blood substitute: A composition lacking erythrocytes and other whole cell components of blood used to replace whole blood in a subject.

Cerebral ischemia or ischemic stroke: A condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes.

Coagulopathy: A medical term for a defect in the body's mechanism for blood clotting.

Ectopic pregnancy: A complication of pregnancy in which the fertilized ovum is implanted in any tissue other than the uterine wall.

Favism: The common name of glucose-6-phosphate dehydrogenase (G6PD) deficiency; an X-linked recessive hereditary disease featuring non-immune hemolytic anemia in response to a number of causes.

Gastrointestinal bleeding: Refers to any form of hemorrhage (loss of blood) in the gastrointestinal tract, from the pharynx to the rectum.

Hemoglobin: The iron-containing oxygen-transport metalloprotein in the red blood cells of the blood in vertebrates and other animals. In humans, the hemoglobin molecule is an assembly of four globular protein subunits. Each subunit is composed of a protein chain tightly associated with a non-protein heme group. Each protein chain arranges into a set of alpha-helix structural segments connected together in a globin fold arrangement, so called because this arrangement is the same folding motif used in other heme/globin proteins such as myoglobin. This folding pattern contains a pocket which strongly binds the heme group.

The heme group consists of an iron (Fe) ion (charged atom) held in a heterocyclic ring, known as a porphyrin. The iron ion, which is the site of oxygen binding, bonds with the four nitrogens in the center of the ring, which all lie in one plane. The iron is also bound strongly to the globular protein via the imidazole ring of a histidine residue below the porphyrin ring. A sixth position can reversibly bind oxygen, completing the octahedral group of six ligands. Oxygen binds in an "end-on bent" geometry where one oxygen atom binds Fe and the other protrudes at an angle. When oxygen is not bound, a very weakly bonded water molecule fills the site, forming a distorted octahedron. The iron ion may either be in the $Fe^{II}$ or $Fe^{III}$ state, but ferrihemoglobin (methemoglobin) ($Fe^{III}$) cannot bind oxygen. In binding, oxygen temporarily oxidizes Fe to ($Fe^{III}$), so iron must exist in the +2 oxidation state in order to bind oxygen. The body reactivates hemoglobin found in the inactive ($Fe^{III}$) state by reducing the iron center.

In adult humans, the most common hemoglobin type is a tetramer (which contains 4 subunit proteins) called hemoglobin A, consisting of two α and two β subunits non-covalently bound, each made of 141 and 146 amino acid residues, respectively. This is denoted as α2β2. The subunits are structurally similar and about the same size. Each subunit has a molecular weight of about 17,000 daltons, for a total molecular weight of the tetramer of about 68,000 daltons. The four polypeptide chains are bound to each other by salt bridges, hydrogen bonds, and hydrophobic interactions.

Oxyhemoglobin is formed during respiration when oxygen binds to the heme component of the protein hemoglobin in red blood cells. This process occurs in the pulmonary capillaries adjacent to the alveoli of the lungs. The oxygen then travels through the blood stream to be delivered to cells where it is utilized in aerobic glycolysis and in the production of ATP by the process of oxidative phosphorylation.

Hemoglobin-based oxygen carrier (HBOC): A transfusable fluid of purified, recombinant and/or modified hemoglobin that functions as an oxygen carrier and can be used as a blood substitute. A number of HBOCs are known and/or in clinical development. Examples of HBOCs include, but are not limited to, DCLHb (HEMASSIST™; Baxter), MP4 (HEMOSPAN™; Sangart), pyridoxylated Hb POE–conjugate (PHP)+catalase & SOD (Apex Biosciences), O—R-Poly-HbA₀ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, Crit Care 8(Suppl 2):S61-S64, 2004; to Lintel Hekkert et al., Am J Physiol Heart Circ Physiol 298:H1103-H1113, 2010; Eisenach, Anesthesiology 111:946-963, 2009).

Hemolysis: The breaking open of red blood cells and the release of hemoglobin into the surrounding fluid.

Hemolytic uremic syndrome (HUS): A disease characterized by microangiopathic hemolytic anemia, acute renal failure and a low platelet count (thrombocytopenia). The classic childhood case of hemolytic uremic syndrome occurs after bloody diarrhea caused by E. coli O157:H7, a strain of E. coli that expresses verotoxin (also called Shiga toxin). The toxin enters the bloodstream, attaches to renal endothelium and initiates an inflammatory reaction leading to acute renal failure and disseminated intravascular coagulation. The fibrin mesh destroys red blood cells and captures thrombocytes, leading to a decrease of both in full blood count. Adult HUS has similar symptoms and pathology but is an uncommon outcome of the following: HIV; antiphospholipid syndrome (associated with Lupus erythematosus and generalized hypercoagulability); post partum renal failure; malignant hypertension; scleroderma; and cancer chemotherapy (mitomycin, cyclosporine, cisplatin and bleomycin). A third category is referred to as Familial hemolytic uremic syndrome. It represents 5-10% of hemolytic uremic syndrome cases and is due to an inherited deficiency leading to uncontrolled complement system activation.

Hemophilia: The name of several hereditary genetic illnesses that impair the body's ability to control coagulation.

Hemorrhage: The loss of blood from the circulatory system. Bleeding can occur internally, where blood leaks from blood vessels inside the body, or externally, either through a natural opening such as the vagina, mouth or rectum, or through a break in the skin.

The average human has around 7 to 8% of their body weight made up of blood. This equates to an average of around 5 liters of blood (5.3 quarts) in a 70 kg (154 lbs.) man. The circulating blood volume is approximately 70 ml/kg of ideal body weight. Thus the average 70 kg male has approximately 5000 ml (5.3 quarts) of circulating blood. Loss of 10-15% of total blood volume can be endured without clinical sequelae in a healthy person, and blood donation typically takes 8-10% of the donor's blood volume. The technique of blood transfusion is used to replace severe quantities of lost blood.

Hemorrhage generally becomes dangerous, or even fatal, when it causes hypovolemia (low blood volume) or hypotension (low blood pressure). In these scenarios various mechanisms come into play to maintain the body's homeostasis. These include the "retro-stress-relaxation" mechanism of cardiac muscle, the baroreceptor reflex and renal and endocrine responses such as the renin-angiotensin-aldosterone system.

Hemorrhage is broken down into four classes by the American College of Surgeons' Advanced Trauma Life Support:

Class I Hemorrhage involves up to 15% of blood volume. There is typically no change in vital signs and fluid resuscitation is not usually necessary.

Class II Hemorrhage involves 15-30% of total blood volume. A patient is often tachycardic (rapid heart beat) with a narrowing of the difference between the systolic and diastolic blood pressures. The body attempts to compensate with peripheral vasoconstriction. Volume resuscitation with crystaloids (saline solution or Lactated Ringer's solution) is all that is typically required. Atypically, blood transfusion may be required.

Class III Hemorrhage involves loss of 30-40% of circulating blood volume. The patient's blood pressure drops, the heart rate increases, peripheral perfusion, such as capillary refill worsens, and the mental status worsens. Fluid resuscitation with crystaloid and blood transfusion are usually necessary.

Class IV Hemorrhage involves loss of >40% of circulating blood volume. The limit of the body's compensation is reached and aggressive resuscitation is required to prevent death.

Hemorrhagic shock: A condition of reduced tissue perfusion, resulting in the inadequate delivery of oxygen and nutrients that are necessary for cellular function. Hypovolemic shock, the most common type, results from a loss of circulating blood volume from clinical etiologies, such as penetrating and blunt trauma, gastrointestinal bleeding, and obstetrical bleeding.

Hypoxaemia: An abnormal deficiency in the concentration of oxygen in arterial blood.

Hypoxia: A pathological condition in which the body as a whole (generalized hypoxia) or region of the body (tissue hypoxia) is deprived of adequate oxygen supply.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Ischemia/reperfusion injury: In addition to the immediate injury that occurs during deprivation of blood flow, ischemic/ reperfusion injury involves tissue injury that occurs after blood flow is restored. Current understanding is that much of this injury is caused by chemical products and free radicals released into the ischemic tissues.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval and the indirect or reperfusion injury that follows. When there is a long duration of ischemia, the direct ischemic damage, resulting from hypoxia, is predominant. For relatively short duration ischemia, the indirect or reperfusion mediated damage becomes increasingly important. In some instances, the injury produced by reperfusion can be more severe than the injury induced by ischemia per se. This pattern of relative contribution of injury from direct and indirect mechanisms has been shown to occur in all organs.

Methemoglobin: The oxidized form of hemoglobin in which the iron in the heme component has been oxidized from the ferrous (+2) to the ferric (+3) state. This renders the hemoglobin molecule incapable of effectively transporting and releasing oxygen to the tissues. Normally, there is about 1% of total hemoglobin in the methemoglobin form.

Microcytosis: A blood disorder characterized by the presence of microcytes (abnormally small red blood cells) in the blood.

Neuroglobin: A member of the vertebrate globin family, believed to be involved in cellular oxygen homeostasis. Neuroglobin is an intracellular hemoprotein expressed in the central and peripheral nervous system, cerebrospinal fluid, retina and endocrine tissues. Neuroglobin is a monomer that reversibly binds oxygen with an affinity higher than that of hemoglobin. It also increases oxygen availability to brain tissue and provides protection under hypoxic or ischemic conditions, potentially limiting brain damage. Neuroglobin is of ancient evolutionary origin, and is homologous to nerve globins of invertebrates. In some embodiments herein, neuroglobin is human neuroglobin (for example, with the amino acid sequence of SEQ ID NO: 8). In some embodiments, neuroglobin is a mutant form of neuroglobin that causes the protein to retain a stable five-coordinate geometry. In particular examples, the mutant neuroglobin comprises a mutation at residue 64 (H64L; the amino acid sequence of which is set forth herein as SEQ ID NO: 9). Nienhaus et al. (*J Biol Chem* 279(22):22944-22952, 2004) describe mutant forms of mouse neuroglobin, including H64L neuroglobin.

Nitrite: The inorganic anion $^-NO_2$ or a salt of nitrous acid $(NO_2^-)$. Nitrites are often highly soluble, and can be oxidized to form nitrates or reduced to form nitric oxide or ammonia. Nitrite may form salts with alkali metals, such as sodium $(NaNO_2$, also known as nitrous acid sodium salt), potassium and lithium, with alkali earth metals, such as calcium, magnesium and barium, with organic bases, such as amine bases, for example, dicyclohexylamine, pyridine, arginine, lysine and the like. Other nitrite salts may be formed from a variety of organic and inorganic bases. In some cases, the nitrite is a salt of an anionic nitrite delivered with a cation, which cation is selected from sodium, potassium, and arginine. Many nitrite salts are commercially available, and/or readily produced using conventional techniques.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peripheral Vascular Disease (PVD): A condition in which the arteries that carry blood to the arms or legs become narrowed or occluded. This interferes with the normal flow of blood, sometimes causing pain but often causing no readily detectable symptoms at all.

The most common cause of PVD is atherosclerosis, a gradual process in which cholesterol and scar tissue build up, forming plaques that occlude the blood vessels. In some cases, PVD may be caused by blood clots that lodge in the arteries and restrict blood flow. PVD affects about one in 20 people over the age of 50, or 8 million people in the United States. More than half the people with PVD experience leg pain, numbness or other symptoms, but many people dismiss these signs as "a normal part of aging" and do not seek medical help. The most common symptom of PVD is painful cramping in the leg or hip, particularly when walking. This symptom, also known as "claudication," occurs when there is not enough blood flowing to the leg muscles during exercise, such that ischemia occurs. The pain typically goes away when the muscles are rested.

Other symptoms may include numbness, tingling or weakness in the leg. In severe cases, people with PVD may experience a burning or aching pain in an extremity such as the foot or toes while resting, or may develop a sore on the leg or foot that does not heal. People with PVD also may experience a cooling or color change in the skin of the legs or feet, or loss of hair on the legs. In extreme cases, untreated PVD can lead to gangrene, a serious condition that may require amputation of a leg, foot or toes. People with PVD are also at higher risk for heart disease and stroke.

Pharmaceutically acceptable carrier: The pharmaceutically acceptable carriers useful in this disclosure are conventional. Parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasma: The fluid portion of the blood in which the formed elements (blood cells) are suspended.

Preeclampsia: A disease of unknown cause in pregnant women, characterized by hypertension, abnormal blood vessels in the placenta, and protein in the urine. It often but not always occurs with gestational diabetes or in diabetics. Additional symptoms may include water retention, leading to swelling in the face, hands and feet, and greater weight gain. Also called toxemia. Preeclampsia can lead to eclampsia if not treated. The only known cure for preeclampsia is delivery of the child.

Preventing or treating a disease: "Preventing" a disease refers to inhibiting the full development of a disease. "Treatment" refers to a therapeutic intervention that ameliorates a sign or symptom of a disease or pathological condition after it has begun to develop.

Reperfusion: Restoration of blood supply to tissue that is ischemic, due to decrease in blood supply. Reperfusion is a procedure for treating infarction or other ischemia, by enabling viable ischemic tissue to recover, thus limiting further necrosis. However, it is thought that reperfusion can itself further damage the ischemic tissue, causing reperfusion injury.

Rhabdomyolysis: The rapid breakdown of skeletal muscle tissue due to traumatic injury, including mechanical, physical or chemical. The principal result is a large release of the creatine phosphokinase enzymes and other cell byproducts into the blood system and acute renal failure due to accumulation of muscle breakdown products, several of which are injurious to the kidney.

Serum: The clear portion of plasma that does not contain fibrinogen, cells or any solid elements.

Sickle cell anemia: A group of genetic disorders caused by sickle hemoglobin. In many forms of the disease, the red blood cells change shape upon deoxygenation because of polymerization of the abnormal sickle hemoglobin. This process damages the red blood cell membrane, and can cause the cells to become stuck in blood vessels. This deprives the downstream tissues of oxygen and causes ischemia and infarction, which may cause organ damage, such as stroke.

Spherocytosis: An auto-hemolytic anemia characterized by the production of red blood cells (or erythrocytes) that are sphere-shaped, rather than donut-shaped.

Subject: Living multi-cellular organisms, including vertebrate organisms, a category that includes both human and non-human mammals.

Thalassemia: An inherited autosomal recessive blood disease. In thalassemia, the genetic defect results in reduced rate of synthesis of one of the globin chains that make up hemoglobin. Reduced synthesis of one of the globin chains causes the formation of abnormal hemoglobin molecules, and this in turn causes the anemia which is the characteristic presenting symptom of the thalassemias.

Therapeutically effective amount: A quantity of compound or composition, for instance, recombinant five-coordinate neuroglobin, sufficient to achieve a desired effect in a subject being treated. For instance, this can be the amount necessary to inhibit or to measurably reduce anemia or other symptom associated with a blood disorder or blood loss. It can also be the amount necessary to restore normal vascular tone and oxygenation to a subject suffering from hemorrhage.

Ulcer: An open sore of the skin, eyes or mucous membrane, often caused, but not exclusively, by an initial abrasion and generally maintained by an inflammation, an infection, and/or medical conditions which impede healing.

Vasoconstriction: The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus, among others.

Vasodilation: A state of increased caliber of the blood vessels, or the act of dilation of a blood vessel, for instance dilation of arterioles leading to increased blood flow to a body part. This can be caused by a specific vasodilator, an agent (for instance, a chemical or biochemical compound) that causes, directly or indirectly, dilation of blood vessels. Such an agent can also be referred to as a vasohypotonic agent, and is said to have vasodilative activity.

Vasospasm: Another cause of stroke; occurs secondary to spasm of blood vessels supplying the brain. This type of stroke typically follows a subarchnoid aneurismal hemorrhage with a delayed development of vasospasm within 2-3 weeks of the bleeding event. A similar type of stroke may complicate sickle cell disease.

Yellow fever: An acute viral disease that is a cause of hemorrhagic illness, particularly in many African and South American countries.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references (including Accession numbers) mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Disclosed herein is the finding that stable five-coordinate neuroglobin can not only bind and release oxygen, but is capable of very rapidly converting nitrite to NO. In particular, a mutant form of human neuroglobin, referred to as H64L neuroglobin (the amino acid sequence of which is set forth herein as SEQ ID NO: 9) is capable of reducing nitrite to NO approximately 2000-times faster than the wild type. Based on these important features of five-coordinate neuroglobin, the use of five-coordinate neuroglobin as a blood substitute is described herein. Many of the previously described blood substitutes are associated with cardiovascular complications due to NO scavenging, thus five-coordinate neuroglobin represents a new therapeutic compound with the potential to alleviate the toxicity associated with current blood substitutes.

Accordingly, provided herein is a method of replacing blood and/or increasing oxygen delivery to tissues in a subject. In some embodiments, the method includes administering to the subject a therapeutically effective amount of neuroglobin with a stable five-coordinate geometry, thereby replacing blood and/or increasing oxygen delivery in the subject.

The subject to be treated, for example, is any subject in need of increasing blood volume or increasing oxygen delivery to tissues. In some embodiments, the subject has or is at risk of developing a disease, disorder or injury associated with a deficiency in red blood cells and/or hemoglobin, or associated with a reduction in oxygen delivery to tissues. In some examples, the disease, disorder or injury comprises a bleeding disorder, a bleeding episode, anemia, shock, ischemia, hypoxia, anoxia, hypoxaemia, a burn, an ulcer, ectopic pregnancy, microcystosis, rhabdomyolysis, hemoglobinopathy, spherocytosis, hemolytic uremic syndrome, thalassemia, disseminating intravascular coagulation, stroke or yellow fever.

In some embodiments, the bleeding episode in the subject to be treated with five-coordinate neuroglobin results from anticoagulant overdose, aneurysm, blood vessel rupture, surgery, traumatic injury, gastrointestinal bleeding, pregnancy, hemorrhage or infection.

In some embodiments, the bleeding disorder in the subject to be treated with five-coordinate neuroglobin comprises hemophilia A, hemophilia B, hemophilia C, Factor VII deficiency, Factor XIII deficiency, a platelet disorder, a coagulopathy, favism, thrombocytopenia, vitamin K deficiency or von Willebrand's disease.

In some embodiments, the anemia in the subject to be treated with five-coordinate neuroglobin comprises microcytic anemia, iron deficiency anemia, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle-cell anemia, warm autoimmune hemolytic anemia or cold agglutinin hemolytic anemia.

In some embodiments, shock in the subject to be treated with five-coordinate neuroglobin comprises septic shock, hemorrhagic shock or hypovolemic shock.

In some embodiments, the subject to be treated suffers from or is at risk of suffering from a disease or condition associated with decreased blood flow, such that increased oxygen and NO delivery is beneficial for treatment of the subject. Examples of diseases or conditions that can be treated using the disclosed methods include, but are not limited to, ischemia, myocardial infarction, stroke, ischemia-reperfusion injury, elevated blood pressure, pulmonary hypertension (including neonatal pulmonary hypertension, primary pulmonary hypertension, and secondary pulmonary hypertension), systemic hypertension, cutaneous ulceration, acute renal failure, chronic renal failure, intravascular thrombosis, an ischemic central nervous system event, vasospasm (such as cerebral artery vasospasm), a hemolytic condition, peripheral vascular disease, trauma, cardiac arrest, general surgery or organ transplantation. Diseases and conditions that benefit from treatment that results in increased NO delivery are described in, for example, PCT Publication No. WO 2005/004884, the disclosure of which is herein incorporated by reference.

The five-coordinate neuroglobin can any type of neuroglobin with a stable five-coordinate geometry that retains the capacity to bind and release oxygen and rapidly reduce nitrite to nitric oxide. For example, the stable five-coordinate neuroglobin can be a mutant and/or recombinant form of neuroglobin. In some embodiments, the amino acid sequence of the stable five-coordinate neuroglobin is at least 85%, at least 90%, at least 95% or at least 99% identical to SEQ ID NO: 9 and comprises a leucine at amino acid residue 64. In particular examples, the amino acid sequence of the stable five-coordinate neuroglobin comprises SEQ ID NO: 9, or consists of SEQ ID NO: 9.

The neuroglobin can further be human neuroglobin or neuroglobin from other species, such as non-human primate neuroglobin, bovine neuroglobin or murine neuroglobin. In particular examples, the five-coordinate neuroglobin is recombinant human neuroglobin.

Five-coordinate neuroglobin can be administered to the subject using any suitable route of administration. In some embodiments, the stable five-coordinate neuroglobin is administered to the subject intravenously. In other embodiments, the stable five-coordinate neuroglobin is administered to the subject intraarterially.

The subject can either be administered stable five-coordinate neuroglobin alone or can be administered a second therapeutic agent or composition, such as a second blood replacement product (also referred to as a blood substitute), a blood product or whole blood.

In some embodiments, the subject is administered a second blood replacement product. In some examples, the second blood replacement product comprises a hemoglobin-based oxygen carrier (HBOC), artificial red blood cells, an oxygen releasing compound, or other blood substitute product. A number of HBOCs are known in the art and are described herein.

In some embodiments, the subject is administered a blood product. In some examples, the blood product comprises packed red blood cells, plasma or serum.

The five-coordinate neuroglobin can be administered to a subject in a single dose (such as a single infusion), or can be administered repeatedly as needed. The dose and dosing schedule can be determined by a medical professional.

In some embodiments of the methods disclosed herein, the subject is a human. In other embodiments, the subject is a non-human animal.

V Five-Coordinate Neuroglobin as a Blood Substitute

The "holy grail" of the transfusion medicine field has been the prospect of developing a cell-free hemoglobin-based oxygen carrier as a red blood cell substitute. Over the last ten years, an estimated investment of more than one billion dollars by the U.S. Department of Defense and pharmaceutical companies has ground to a halt based on a previously unsuspected reaction: the scavenging reaction of endothelial derived NO with the hemoglobins. This scavenging of NO has adverse consequences on vascular function because NO is a critical regulator of blood vessel homeostasis by producing tonic vasodilation, inhibiting thrombosis and platelet activation, and down-regulating the expression of endothelial adhesion molecules. Therefore, the complete scavenging of NO by infused hemoglobin solutions in clinical trials resulted in hypertension, renal failure, myocardial infarction and possible increases in mortality.

Second generation hemoglobin molecules have been developed that are decorated with macromolecules to increase their molecular size, and while these products have reduced the hypertensive effects to some extent, the physiological perturbations of NO depletion remain problematic. Thus, a need exists for an oxygen carrier molecule that can bind and deliver molecular oxygen and generate NO, rather than simply destroying it. Such a molecule would offer the potential to solve this central problem in the blood substitute field. The data disclosed herein indicate that five-coordinate neuroglobin meets these criteria. Mutation of the proximal histidine (the histidine at residue 64, numbered with reference to SEQ ID NO: 8) produces a unique molecule that rapidly generates NO from nitrite at enzyme-like rates, but also stably binds and releases oxygen.

Thus, described herein is the use of stable five-coordinate hemoglobin as a blood substitute. Provided is a method of replacing blood and/or increasing oxygen delivery to tissues in a subject. In some embodiments, the method includes administering to the subject a therapeutically effective amount of neuroglobin with a stable five-coordinate geometry, thereby replacing blood and/or increasing oxygen delivery in the subject. Five-coordinate neuroglobin is contemplated for use as a blood substitute for the treatment of a number of diseases, disorders or injuries that result in a loss of blood volume and/or a deficiency of oxygen delivery to tissues.

In many cases, the subject to be treated with five-coordinate neuroglobin has or is at risk of developing a disease, disorder or injury associated with a deficiency in red blood cells and/or hemoglobin, or associated with a reduction in oxygen delivery to tissues. Exemplary diseases, disorders and injuries include, but are not limited to bleeding disorders (such as hemophilia A, hemophilia B, hemophilia C, Factor VII deficiency, Factor XIII deficiency, a platelet disorder, a coagulopathy, favism, thrombocytopenia, vitamin K deficiency or von Willebrand's disease), bleeding episodes (such as a bleeding episode that results from anticoagulant overdose, aneurysm, blood vessel rupture, surgery, traumatic injury, gastrointestinal bleeding, pregnancy, hemorrhage or infection), anemia (such as microcytic anemia, iron deficiency anemia, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle-cell anemia, warm autoimmune hemolytic anemia or cold agglutinin hemolytic anemia), shock (such as septic shock, hemorrhagic shock or hypovolemic shock), ischemia, hypoxia, anoxia, hypoxaemia, a burn, an ulcer, ectopic pregnancy, microcystosis, rhabdomyolysis, hemoglobinopathy, spherocytosis, hemolytic uremic syndrome, thalassemia, disseminating intravascular coagulation, stroke or yellow fever.

In some embodiments, the subject to be treated suffers from or is at risk of suffering from a disease or condition associated with decreased blood flow, such as myocardial infarction, stroke, ischemia-reperfusion injury, pulmonary hypertension or vasospasm.

Five-coordinate neuroglobin can be administered to the subject using any suitable route of administration, such as intravenous or intraarterial. In addition, the subject can either be administered stable five-coordinate neuroglobin as a single therapeutic compound or the subject can be treated with a second (or additional) therapeutic agent or composition. For example, five-coordinate neuroglobin can be administered in combination with a second blood substitute, a blood product or whole blood. As used herein, "co-administration" of a second therapeutic composition is not limited to administration at the same time as five-coordinate neuroglobin or in the same composition as five-coordinate neuroglobin, but rather includes administration prior to and following administration of five-coordinate neuroglobin. For example, administration of the second therapeutic agent or composition can occur 1 hour, 2 hours, 8 hours, 12 hours, 24 hours, 2 days, 3 days, 4 days, 5 days, 6 days, 1 week, 2 weeks, 3 weeks or 4 weeks prior to or following administration of five-coordinate neuroglobin.

In some cases, the subject is co-administered a second blood replacement product, such as a blood expander (to increase blood volume) or an oxygen therapeutic (such as an HBOC or PFC). In some examples, the second blood replacement product comprises a HBOC, artificial red blood cells or an oxygen releasing compound. A number of HBOCs are known in the art and are described herein. Non-limiting examples of HBOCs include DCLHb (HEMASSIST™; Baxter), MP4 (HEMOSPAN™; Sangart), pyridoxylated Hb POE–conjugate (PHP)+catalase & SOD (Apex Biosciences), O—R-PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8(Suppl 2):S61-S64, 2004; to Lintel Hekkert et al., *Am J Physiol Heart Circ Physiol* 298:H1103-H1113, 2010; Eisenach, *Anesthesiology* 111:946-963, 2009).

In some cases, the subject is co-administered a blood product, such as packed red blood cells, plasma or serum.

The five-coordinate neuroglobin can be administered to a subject in a single dose (such as a single infusion), or can be administered repeatedly as needed. The dose and dosing schedule can be determined by a medical professional.

The actual dosage of five-coordinate neuroglobin will vary according to factors such as the type and severity of disease, disorder or injury and particular status of the subject (for example, the subject's age, size, fitness, extent of symptoms, susceptibility factors, and the like), time and route of administration, other drugs or treatments being administered concurrently. Dosage regimens can be adjusted to provide an optimum therapeutic response. A therapeutically effective amount is also one in which any toxic or detrimental side effects of the blood substitute and/or other therapeutic agent is outweighed in clinical terms by therapeutically beneficial effects.

The following examples are provided to illustrate certain particular features and/or embodiments. These examples should not be construed to limit the disclosure to the particular features or embodiments described.

EXAMPLES

Example 1

Material and Methods

This example describes the experimental procedures used for the studies described in Example 2.

Reagents and General Methods

All reagents were purchased from Sigma-Aldrich unless otherwise specified. UV-visible spectra and kinetic data were recorded on an HP8453 UV-Vis spectrophotometer (Hewlett-Packard) using 1 cm path length quartz or special optical glass cuvettes. Superdex 5200 gel filtration columns were purchased from GE Healthcare Life Science. Horse heart myoglobin (Mb) was purified by passing through a Sephadex™ G-25 gel filtration column and elution with 100 mM potassium phosphate buffer (pH 7.4). Solutions of sodium dithionite and nitrite were prepared and kept at 25° C. with argon degassed 0.1 M phosphate buffer (pH 7.4) under inert gas.

Standards Sample Preparation

Neuroglobin was oxidized with excess potassium ferricyanide or reduced by incubation with 500 mM sodium dithionite; excess reagents were removed by passing the mixture through two sequential Sephadex™ G-25 desalting columns. Met-Ngb concentrations were estimated by measuring the absorbance of the heme Soret band using $\epsilon_{414}=129$ mM$^{-1}$ cm$^{-1}$. Standard reference species of recombinant Ngb for spectral deconvolution were prepared following procedures previously described for hemoglobins (Shiva et al., *Circ Res* 100:654-661, 2007; Grubina et al., *J Biol Chem* 282:12916-12927, 2007). Reference spectra were recorded for deoxy-Ngb, iron-nitrosyl-Ngb, met-Ngb, and oxy-Ngb. When necessary, anaerobic reduced Ngb samples were prepared in glovebox under a 2%-4% H$_2$ atmosphere of catalyst-deoxygenated nitrogen, collected directly in cuvettes and sealed with rubber septa inside the glovebox. To reduce the intramolecular Ngb disulfide bond, Ngb solutions were dialyzed in PBS containing 10 mM DTT dissolved in degassed 100 mM HEPES or phosphate buffer and 0.5 mM EDTA as previously described (Nicolis et al., *Biochem J* 407:89-99, 2007). The number of accessible thiol groups per heme was measured by the 4-PDS assay (Grassetti and Murray, *Arch Biochem Biophys* 119:41-49, 1967).

Cloning, Expression and Purification of Recombinant Ngb

Restriction digestions, ligation, transformation, cloning, bacterial growth and isolation of DNA fragments were performed using standard techniques. For the expression of the 151 amino acid polypeptide of human Ngb, the cDNA SC122910 (GenBank Accession No. NM_021257; SEQ ID NO: 7) was cloned in BL21(DE3)pLysS(pET28a). Cells were grown in LB broth containing 30 μg/ml kanamycin and 25 μg/ml chloramphenicol, expression was induced with 1 mM IPTG and carried out for 4 hours at 37° C. including δ-aminolevulinic acid (0.4 mM) in the media. Purification was carried out as previously described with minor modifications (Burmester et al., *Nature* 407:520-523, 2000). To increase purification yield, human Ngb cDNA was fused with a 6× His tag in the N-terminus and cloned into pET28a. Proteins were overexpressed in *E. coli* strain BL21(DE3). Purification of His tagged human Ngb was performed using Ni-NTA-agarose (Qiagen) affinity column according to the manufacturer's instructions. His tagged Ngb was eluted with 200 mM imidazole after washing with 20 mM imidazole. The eluted protein was dialyzed against PBS at 4° C., concentrated with a 10 kD cutoff filter and stored in aliquots at −80° C. The additional amino acids at the N-terminus of His tagged Ngb were removed using a thrombin cleavage capture kit (Novagen). The purity of each recombinant Ngb batch prepared was assessed by SDS-PAGE and UV-visible spectroscopy.

Mutagenesis of Recombinant Ngb

Site directed mutagenesis was performed using QuikChange™ II kit (Stratagene). The oligonucleotides for mutations C46A, C55A and H64L are shown in Table 1 below.

TABLE 1

Oligonucleotides used to perform site-directed mutagenesis of Ngb

| Ngb Mutant | Sequence | SEQ ID NO: |
|---|---|---|
| C46A | CTCTTCCAGTACAACGCCCGCCAGTTCTCCAG | 1 |
| C46A | CTGGAGAACTGGCGGGCGTTGTACTGGAAGAG | 2 |
| C55A | TCCAGCCCAGAGGACGCTCTCTCCTCGCCTGAG | 3 |
| C55A | CTCAGGCGAGGAGAGAGCGTCCTCTGGGCTGGA | 4 |
| H64L | CTGAGTTCCTGGACCTGATCAGGAAGGTGATGC | 5 |
| H64L | GCATCACCTTCCTGATCAGGTCCAGGAACTCAG | 6 |

The template used for C46A and C55A was pCMV-1A and for H64L was pET28a. Clones were sequenced to confirm the desired mutations. Expression and purification of mutant Ngb were carried out using the same procedures as for wild type Ngb.

Anaerobic Reactions of Globins with Excess Nitrite

Reaction kinetics of known amounts of Mb or Ngb with nitrite were monitored by absorption spectroscopy for the indicated time in a cuvette in the presence or absence of 2-4 mM sodium dithionite. All reactions were run at 25° C. or 37° C. in 0.1 M phosphate buffer at controlled pH. Previously deoxygenated nitrite was added, using an airtight syringe, to a sealed anaerobic cuvette to initiate the reaction. Oxygen contamination was prevented by application of positive argon pressure without a channel for gas escape. Concentrations of single species during reactions were determined by least squares deconvolution of the visible absorption spectrum into standard reference spectra using Microsoft Excel analysis. OxyNgb was included to confirm successful deoxygenation before the reaction. To vary pH, deoxy-Ngb and nitrite were prepared in phosphate buffer adjusted to the target pH values. Fast kinetic studies were performed using an Applied Photophysics DX-17 stopped-flow instrument equipped with rapid-scanning diode array detection. Experiments were carried out at 25° C. by rapidly mixing a solution of reduced deoxy-Ngb containing 2 mM dithionite with a known solution of nitrite at controlled pH. To determine bimolecular rate constants all reactions were analyzed with Pro-K software (Applied Photophysics) using singular value decomposition followed by fitting of the reduced data matrix to a pseudo-first order kinetic model.

Model of the Wild-Type Human Ngb Structure

Crystallization of the wild-type human Ngb is hindered by aggregation and precipitation problems. Mutation of the three cysteine residues yielded a protein suitable for crystallization studies (Pesce et al., *Structure* 11:1087-1095, 2003). The reported structure (PDB 1OJ6) thus includes the mutations Cys46Gly, Cys55Ser and Cys120Ser. To assess the possible structure of the wild type enzyme a homology model was built using the Swiss-Model server (Schwede et al., *Nucleic Acids Res* 31:3381-3385, 2003) with the sequence of the wild type Ngb and the available human structure as template. The coordinates of the heme molecule were copied from the 1OJ6 structure.

Determination of the Midpoint Redox Potential of the Thiol/Disulfide Couple in Ngb Wild-type and C55A mutant Ngb (50-60 μM) were incubated at 37° C. in anaerobic glove box with solutions containing various ratios of reduced (GSH) and oxidized (GSSG) glutathione, with the total GSH and GSSG concentration fixed at 25 mM in 0.1 M phosphate buffer pH=7.0. The GSH/GSSG ratio was varied to establish a gradient of redox potentials between −130 and −250 mV, calculated by the Nernst equation according to a midpoint reduction potential of −240 mV (Yi et al., *J Biol Chem* 284:20556-20561, 2009). After at least 1 hour incubation, glutathione was removed by passage through a G25 column and Ngb was reacted immediately with 10 mM nitrite in 0.1 M phosphate buffer pH=7.0 as described above. The observed rate constant determined at each glutathione ratio was fitted using the Nernst equation and the midpoint reduction potential of the thiol/disulfide couple of Ngb calculated.

Determination of Nitrite Binding Constants

To determine the binding constant of nitrite to metNgb, 10 µM wild type and mutant Ngb in 200 mM phosphate buffer, pH 7.4, were incubated in a cuvette at 25° C. with increasing concentrations of nitrite and the UV—visible spectra were recorded after each increase in nitrite concentration. The constant $K_D$ for each protein was determined by interpolation of the absorbance data following procedures in Nicolis et al. (*Biochem J* 407:89-99, 2007).

NMR Spectroscopy $^1$H NMR spectra in $^1$H$_2$O were collected at 29 C on a Bruker DRX-600 NMR spectrometer operating at 599.79 MHz with a 5 mm triple resonance probe using a water presaturation pulse sequence with 1 s irradiation time. Samples of wild type and mutant 250-300 µM met-Ngb were prepared in 0.1M phosphate buffer pH 7.4. Typically 1024 transients were averaged, using 90 degree pulses, spectral width of 80 ppm and 16K time domain points. Spectra are referenced indirectly through the resonance of the water, which occurs at 4.76 ppm downfield from the methyl resonance of DSS (2,2-dimethyl-2-silapentane-5-sulfonate).

Electron Paramagnetic Resonance Spectroscopy

Iron nitrosyl species were measured by EPR spectroscopy using a Bruker EMX 10/12 spectrometer operating at 9.4 GHz, 5-G modulation, 10.1-milliwatt power, 327.68-ms time constant and 163.84-s scan over 600 G at 110 K as described previously (Basu et al., *J Biol Chem* 283:32590-32597, 2008; Azarov et al., *J. Biol. Chem.* 280:39024-38032, 2005). The concentrations of Mb and Ngb species were determined by performing the double integral calculation and comparing to standard samples.

Direct Measurement of NO Release

Deoxy-Ngb (final concentration 20 µM) was injected in 3 ml anaerobic 100 mM phosphate buffer, pH 7.4 in a vessel purged with helium gas and connected in line to an NO chemiluminescence analyzer (Sievers, GE Analytical Instruments). Once a stable baseline was established Ngb was reacted with a known amount of nitrite as previously described (Huang et al., *J Clin Invest* 115:2099-2107, 2005).

Isolation and Respiration of Isolated Mitochondria with Neuroglobin Molecules

Mitochondria were isolated from the livers of male Sprague Dawley rats and incubated with wild-type or mutant Ngb proteins in a sealed, stirred chamber at 37° C. State 3 respiration was stimulated with succinate (15 mM) and ADP (1 mM) and oxygen consumption was measured with a Clark-type oxygen electrode. To measure inhibition of respiration in hypoxic conditions, respiring mitochondria were allowed to consume oxygen until the chamber became anoxic and then the chamber lid was removed to allow the diffusion of air back into the chamber. The rate of mitochondrial respiration was greater than the rate of oxygen entering the chamber such that the oxygen electrode trace remained at zero while the mitochondria were respiring. Nitrite was added to the chamber prior to the removal of the lid and deviation of the oxygen trace from a zero reading signified a decrease in respiration rate. All experiments were performed under conditions where substrates were not limiting. The extent of respiratory inhibition was quantified by measuring the time from equilibration of the mitochondria with air to the time when the oxygen trace deviated from zero. This time to inhibition was expressed as a percentage of maximal inhibition, where 100% inhibition was defined as the time to inhibition in the presence of cyanide and the time to the exhaustion of substrates was used as a measure of 0% inhibition. Similar experiments were performed with SHSY5Y cells suspended in the respirometer and treated with the uncoupler FCCP (5 µM) to measure hypoxic inhibition of cellular respiration.

Immunoblotting of Neuroglobin Expression in SHSY5Y Neuronal Cells

Equal amounts of denatured total proteins (25 µg) from the SHSY5Y neuronal cells expressing GFP vector, wild type and H64L mutant Ngb, were subjected to 4-15% SDS-polyacrylamide gradient gels and immunoblotted with anti-GFP monoclonal antibody (Santa Cruz Biotechnologies, Inc) and scanned with the Odyssey imaging system (LI-COR Biosciences).

Determination of cGMP in SHSY5Y Neuronal Cells

SHSY5Y cells, expressing the GFP vector, wild type Ngb or H64L mutant Ngb were plated on Corning® CellBIND® Surface 100 mm culture dishes at a concentration of 5-7.5× $10^5$ cells/plate and grown to 80-90% confluence. After four days of growth, the cells were incubated for 6 hours under hypoxic conditions (1% oxygen). Following hypoxic treatment, the cGMP levels were measured using the cyclic GMP EIA Kit (Cayman Chemicals catalog #581021) according to the manufacturer's instructions. Protein levels were measured and used to normalize results.

Statistical Analysis

Each experiment was performed at least in triplicate and values are representative of two or more independent determinations using different batches of protein purified separately. Data were analyzed using Origin 8.0 (OriginLab) and expressed as mean±standard deviation of the mean. Analysis for statistically significant differences among mean values was done, when applicable, using the Student's t-test with a value of p<0.05 considered as significant.

Example 2

Human Neuroglobin Functions as a Redox Regulated Nitrite Reductase

This example describes the finding that a stable five-coordinate neuroglobin mutant (H64L) reduces nitrite to NO approximately 2000-times faster than the wild type neuroglobin, and mutation of either C55 or C46 to alanine stabilizes the six-coordinate structure and slows nitrite reduction.

Nitrite is Reduced to NO via Reaction with Deoxygenated Human Neuroglobin

Figure 7A:
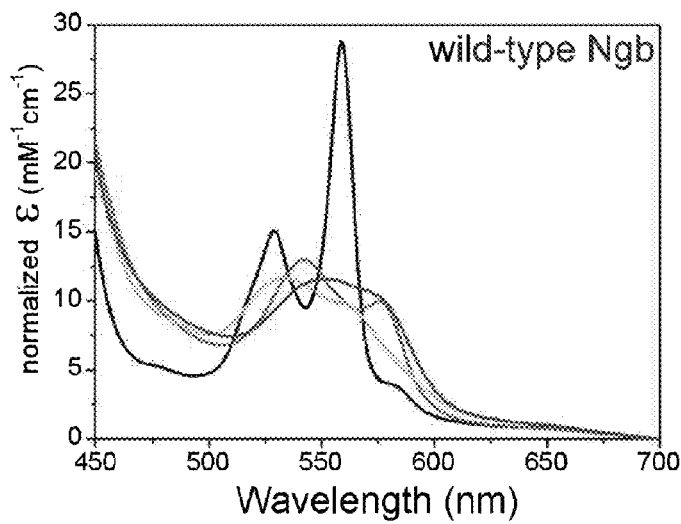
FIG. 7: Visible standard reference spectra of neuroglobin and myoglobin proteins utilized for deconvolution. Visible spectra of deoxy-, oxy-, met-, and iron-nitrosyl-human wild-type Ngb (A), H64L Ngb (B) and myoglobin (C). Spectra were normalized at 700 nm and utilized for least-squares analysis of multi-component spectra.

In order to examine the reaction of nitrite with neuroglobin, recombinant human neuroglobin was expressed and purified. Spectrophotometric analysis of His-tagged or untagged proteins confirmed the six-coordinate heme structure in both the ferrous and ferric states of Ngb, with visible α and β peaks around the 550 nm wavelength (FIG. 7A). Ferrous deoxy-Ngb was prepared in an anaerobic glove box as detailed in Example 1 and the visible spectra of the reaction was recorded between 10 µM deoxy-Ngb and 10 mM nitrite at 25° C. at constant intervals in a sealed air tight cuvette under external argon pressure (FIG. 1A). The time-dependent changes of deoxy-Ngb, ferric met-Ngb and iron-nitrosyl-Ngb ($Fe^{+2}$—NO) species (FIG. 1B) were calculated by least squares deconvolution of the reaction spectra using standard reference spectra (FIG. 7A). In an anaerobic environment nitrite is reduced to NO according to equation 1 and the NO generated has very high affinity ($k_{on}=10^8 M^{-1} s^{-1}$) for the ferrous Ngb heme thus yielding iron-nitrosyl-heme ($Fe^{+2}$—NO) as a final reaction product (equation 2).

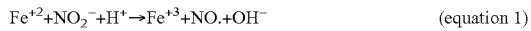

$$Fe^{+2}+NO_2^-+H^+ \rightarrow Fe^{+3}+NO.+OH^- \quad \text{(equation 1)}$$

$$NO.+Fe^{+2} \rightarrow Fe^{+2}\text{—NO} \quad \text{(equation 2)}$$

Figure 1A:
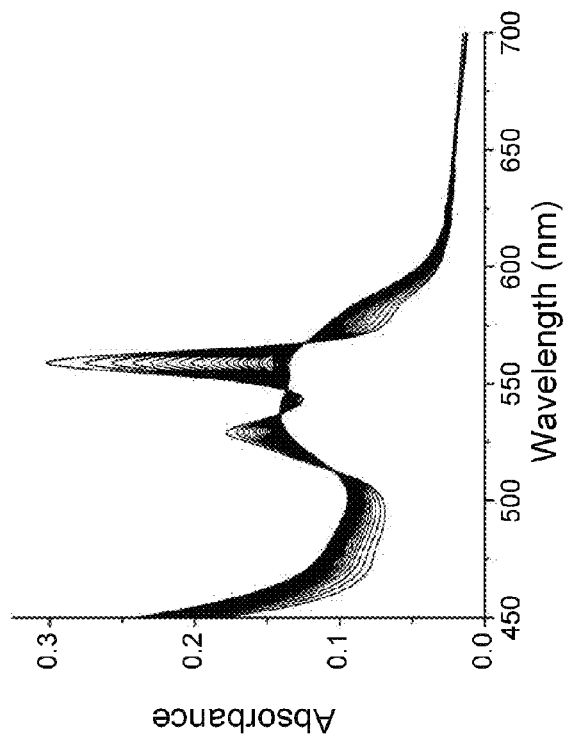

A reaction stoichiometry consistent with the reaction of nitrite with hemoglobin or myoglobin was observed, with two deoxy-Ngb molecules forming one iron-nitrosyl-Ngb and one ferric Ngb (FIG. 1B). Analysis of the instantaneous bimolecular rate constant (BRC) over time indicated that the reaction of nitrite with Ngb at pH 7.4 proceeds at $0.12 \pm 0.02$ $M^{-1}$ $s^{-1}$ at 25° C. ($0.26 \pm 0.02$ $M^{-1}$ $s^{-1}$ at 37° C.). A recent study (Petersen et al., *J Inorg Biochem* 102:1777-1782, 2008) reported that the reaction of deoxy mouse neuroglobin with nitrite in the range 7-230 μM generated ferric met-Ngb in excess of ferrous nitrosyl-Ngb at apparent second-order rate constant of $5.1 \pm 0.4$ $M^{-1}$ $s^{-1}$; however, the current experimental conditions with human neuroglobin differ considerably.

Figure 1D:
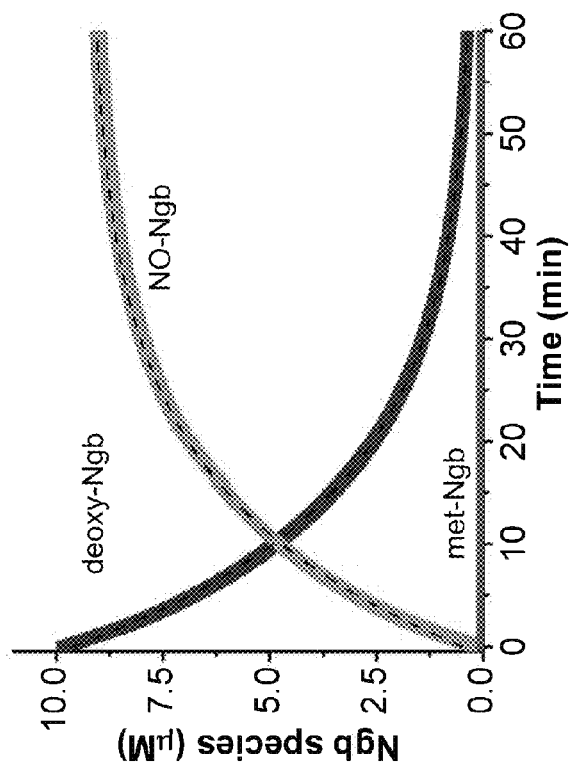
Figure 1C:
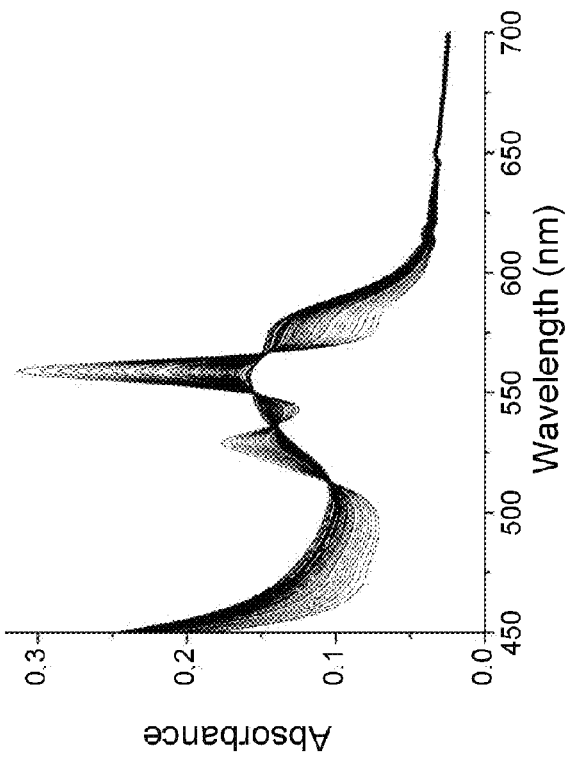
Figure 1F:
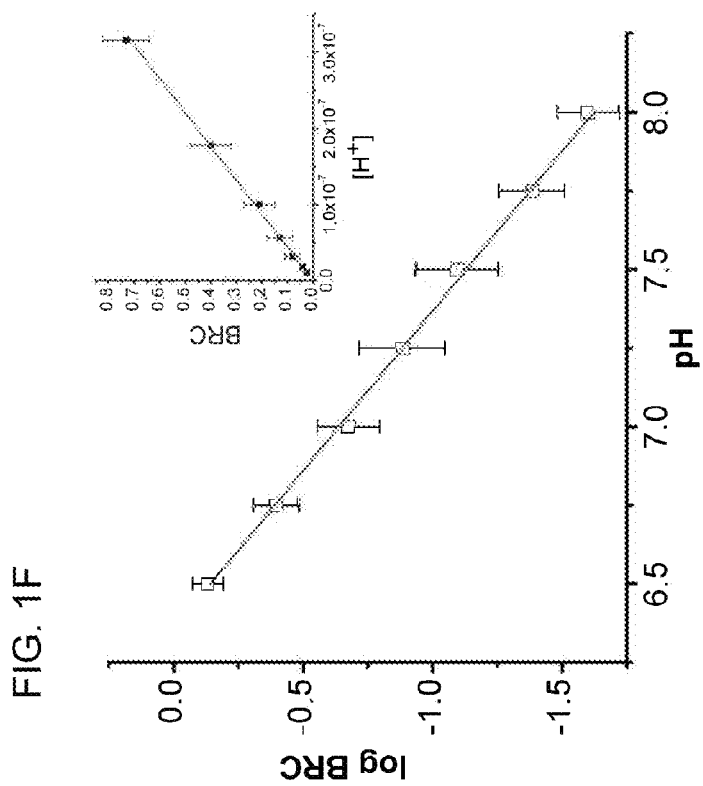
Figure 1E:
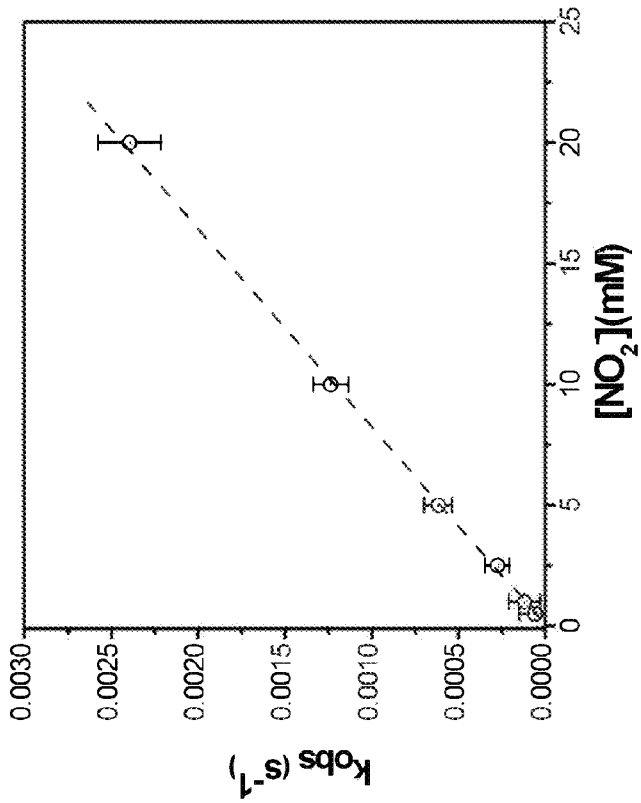
Figure 8A:
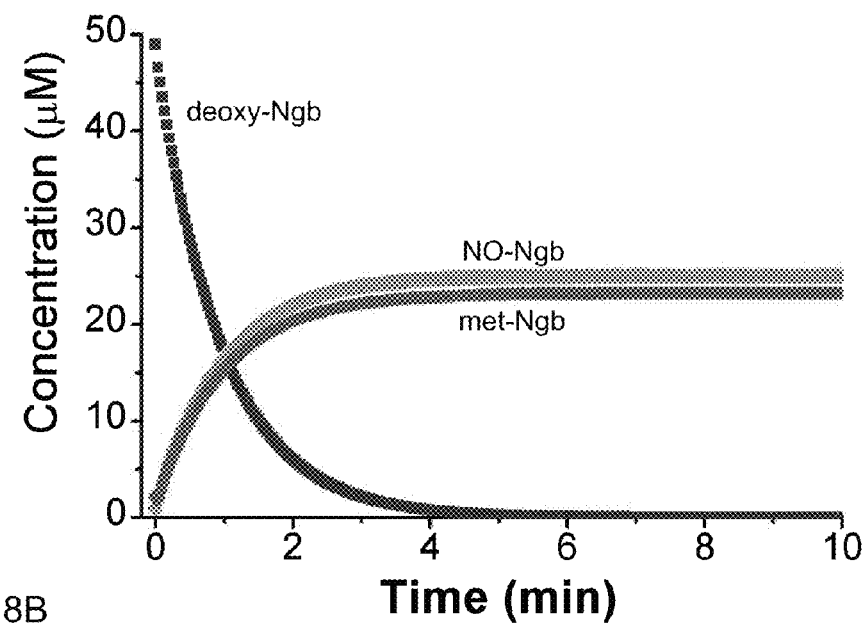
FIG. 8: Anaerobic reaction of myoglobin (Mb) with nitrite in the absence and in the presence of dithionite. (A) Time-dependent changes of deoxy-Mb, iron nitrosyl-Mb and total met-Mb concentration during the reaction of 50 μM deoxy-Mb with 2.5 mM nitrite. (B) Time-dependent changes of deoxy-Mb, iron nitrosyl-Mb and total met-Mb concentration during the reaction of 50 μM deoxy-Mb with 2.5 mM nitrite in the presence of 2 mM dithionite. Myoglobin reacts with nitrite with a BRC of 2.9±0.2 M$^{-1}$ sec$^{-1}$ in 100 mM phosphate buffer containing mM EDTA, pH 7.4 and at 25° C.
Figure 8B:
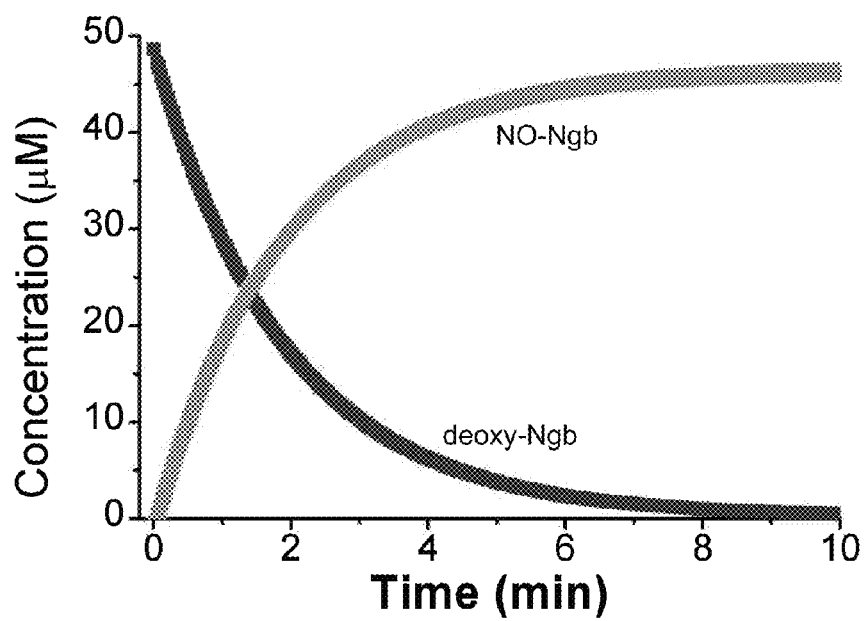

Both Salhany and the Gladwin group have shown (Grubina et al., *J Biol Chem* 283(6):3628-3638, 2008; Salhany, *Biochemistry* 47:6059-6072, 2008) that the reaction of nitrite with hemoglobin in the presence of dithionite proceeds via equation 1-2, but the ferric heme that is formed is reduced back to the ferrous form to continue the reaction. Thus iron-nitrosyl-heme forms at the same rate as deoxyheme is consumed and the overall stoichiometry is one deoxy-Ngb forming one iron-nitrosyl-Ngb. Performing the reaction in the presence of dithionite limits the auto-oxidation of the ferrous heme prior to the reaction with nitrite and allows for facile assessments of anaerobic reaction mechanisms and kinetics. By complementary studies using myoglobin it was verified that the rate-limiting step of the reaction in the presence of dithionite is the heme iron catalyzed conversion of nitrite to NO (FIGS. 8A and 8B). Then the reaction of anaerobic nitrite and deoxy-Ngb (10 mM and 10 μM respectively) was performed as described above in the presence of 3 mM excess dithionite at pH 7.4 in 100 mM phosphate buffer (FIGS. 1C and 1D). The stoichiometry was consistent with one deoxy-Ngb forming one iron-nitrosyl-Ngb and the calculated BRC was $0.11 \pm 0.01$ $M^{-1}$ $sec^{-1}$, in accordance with the BRC value obtained in the absence of dithionite. The reactivity of deoxy-Ngb with nitrite in the concentration range 0.25-20 mM (FIG. 1E) was further investigated. The second-order bimolecular rate constant derived from the linear fit of the observed rate constants versus nitrite concentration is $0.12 \pm 0.02$ $M^{-1}$ $sec^{-1}$ in agreement with the calculated instantaneous BRC.

Proton Dependence of the Nitrite Reductase Reaction with Neuroglobin

It was next explored whether deoxy-Ngb dependent nitrite reduction requires a proton (equation 1). The pH dependence of the bimolecular rate constant of the nitrite reductase reaction near the physiological range (pH 6.5-8.0) (FIG. 1F) was determined. It was found that increasing concentration of protons accelerate the reaction by 10-fold for each pH unit decrease. The slope of the linear fit, which represents the order of rate dependence on [$H^+$] is 0.96, close to the ideal 1.0, and it extends through the zero point (FIG. 1F inset) indicating the requirement for one proton in the reaction. It was concluded that the reaction constitutes a concerted electron and proton transfer to nitrite to form NO analogous to bacterial nitrite reductase.

Figure 2A:
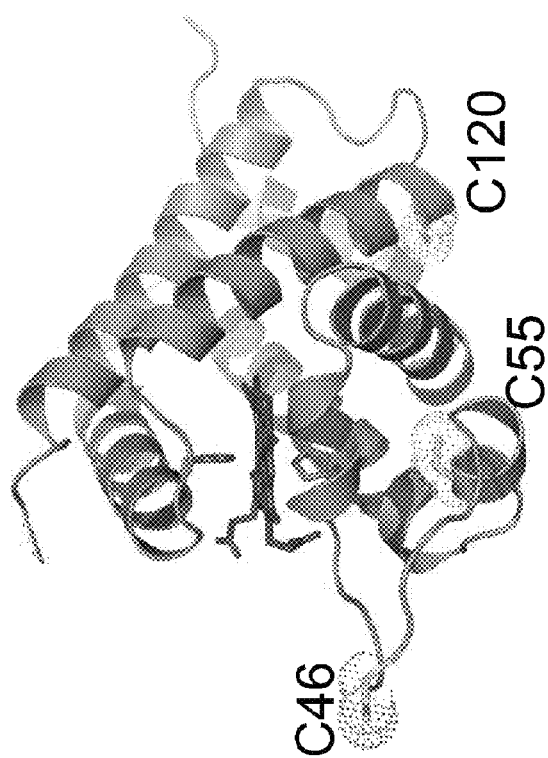
FIG. 2: Redox state of cysteines 46 and 55 modulates nitrite reductase reactivity. (A) Model of the wild-type human neuroglobin structure with indicated reduced cysteines C46, C55 and C120. (B) Determination of the number of reduced cysteines by the 4-PDS assay (see Example 1). (C) Comparison of the decrease of deoxy-Ngb and the formation of iron-nitrosyl Ngb over time for wild-type Ngb with oxidized (SS) and reduced (SH) thiol, C46A and C55A mutant Ngb. (D) Observed nitrite reductase rate constants versus determined redox potentials. The midpoint redox potential of the thiol/disulfide couple in wild-type Ngb is $-194 \pm 3$ mV. (E) Comparison of the NMR spectrum of wild type and C55A mutant met-Ngb. (F) Nitrite binding affinity constant for wild-type, DTT cysteines reduced and C55A mutant Ngb.
Figure 2B:
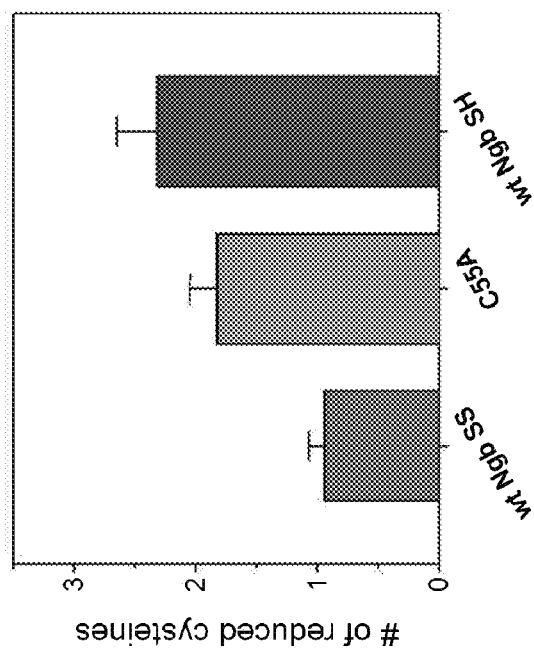

Surface Cysteines C46 and C55 Regulate the Heme Pocket Coordination and the Rate of Nitrite Reduction to NO The control of the six-to-five coordinate iron heme transition is the subject of much interest in the hexa-coordinate globin field (Nadra et al., *Proteins* 71:695-705, 2008; Basu et al., *J Biol Chem* 283:32590-32597, 2008; Bykova et al., *Biochem Biophys Res Commun* 347:301-309, 2006; Smagghe et al., *Biochemistry* 45:561-570, 2006; Fago et al., *J Inorg Biochem* 100:1339-1343, 2006). Unlike most other globins, human Ngb displays 3 conserved cysteines (notable exception being mouse Ngb) at positions 46, 55 and 120 located on the protein surface as shown in the wild type thiol reduced human Ngb structure model (FIG. 2A). Investigators have identified a role for cysteines 46 and 55 in the regulation of the heme ligand binding equilibrium. These cysteines form an intra-molecular disulfide bond (Wakasugi et al., *J Biol Chem* 278:36505-36512, 2003), which influences the position of the E-helix containing the distal histidine (Hamdane et al., *J Biol Chem* 278:51713-51721, 2003). Reduction of the disulfide bond allows additional structural freedom in the orientation of the E-helix (FIG. 2A), that leads to an increased proportion of molecules in the six-coordinate state and thus reduced oxygen and nitrite binding affinities (Hamdane et al., *J Biol Chem* 278:51713-51721, 2003; Nicolis et al., *Biochem J* 407: 89-99, 2007). Using the 4-PDS assay, the number of accessible thiols per heme in wild-type neuroglobin, as purified and reduced by DTT, and in the C55 to alanine mutant neuroglobin, was determined (FIG. 2B). The results are consistent with the quantitative formation of a disulfide bond during protein purification and the presence of the single reduced Cys120 in the oxidized thiol form.

Figure 2D:
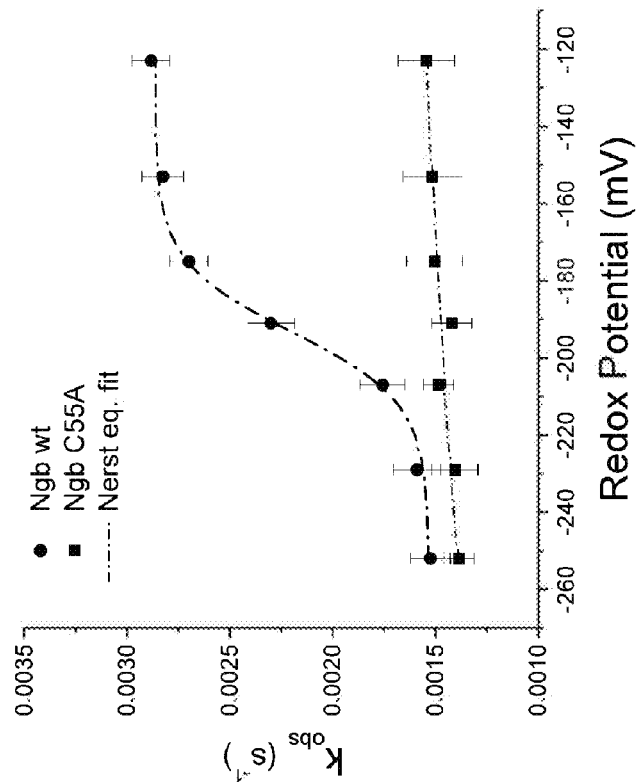
Figure 2C:
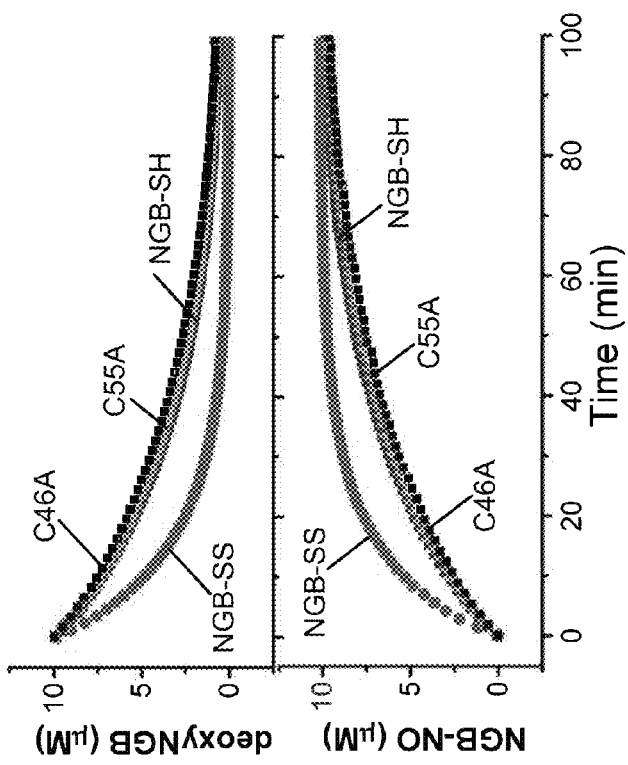

To determine if the rate of nitrite reduction is influenced by the redox state of cysteines 46 and 55, the cysteines were first reduced by incubation with 10 mM dithiothreitol (DTT) and then the rate of nitrite reduction was measured after anaerobic DTT removal. FIG. 2C shows that reduction of the disulfide bond slows down the rate by about 2-fold ($0.062 \pm 0.005$ $M^{-1}$ $sec^{-1}$ at 25° C., pH 7.4). To directly test the hypothesis that disulfide bridge reduction affects the nitrite reactivity of neuroglobin, recombinant mutants with cysteine 55 or 46 replaced by alanine (C55A and C46A), which slowed down the rate of nitrite reduction to similar rates observed with Ngb having fully reduced cysteines, were produced (FIG. 2C). Physiological Redox Control of the C46-055 Disulfide Bond Regulates the Rate of Nitrite Reduction to NO To determine if the formation of a disulfide bond between Cys 46 and 55 is redox-regulated within the physiological range of cellular redox status, wild-type and C55A mutant Ngb were incubated with increasing ratios of reduced/oxidized glutathione that established a gradient of ambient redox potentials. After 60 minutes incubation, the rates of nitrite reduction were measured after removal of glutathione by passage through a G25 column (FIG. 2D). It was found that there was a sudden and substantial drop in the observed nitrite reductase rate constants ($k_{obs}$) with decreasing redox potential only for the wild-type protein. Fitting the data to the Nernst equation provided a midpoint reduction potential of the C46/C55 thiol/disulfide redox couple of $-194 \pm 3$ mV. This value is within the range of cellular redox potentials (*E. Coli* cytosol $E_0=-280$ mV (Schafer and Buettner, *Free Radic Biol Med* 30:1191-1212, 2001)).

To directly examine whether the cysteines redox state causes changes in heme pocket molecular and electronic structure, the NMR spectrum of wild type and C55A mutant met-Ngb (FIG. 2E) was compared. Characteristic NMR signals for the heme methyls are visible in the spectral regions around 36 ppm, 23 ppm and 20 to 12 ppm and were assigned by comparison with the published spectra (Du et al., *J Am Chem Soc* 125:8080-8081, 2003; Xu et al., *J Inorg Biochem* 103:1693-1701, 2009). The two spectra are largely similar but a few marked differences in the positions of several heme methyl resonances (M8-B, M5-A, M1-A, M5-B) as well of several hyperfine shifted resonances between 18 and 12 ppm (FIG. 2E, region marked with an asterisk) were assigned. Also several unassigned ring current shifted resonances around −2 ppm are different. It was concluded that the thiol mutation C55A clearly affects the geometry of the heme pocket environment.

The nitrite binding affinity constant for the oxidized and reduced cysteines of wild type and C55A mutant met-Ngb were determined by difference spectra titration (FIG. 2F). The calculated dissociation constants ($K_D$) reported in Table 2 confirmed the influence of the cysteine redox state on the nitrite binding affinity to the heme iron. During these experiments it was also observed that met-Ngb very slowly reacts with nitrite to produce nitrosyl-Ngb (BMC reported in Table 2). The slow rates of reaction produce a detectable spectroscopic effect only at high nitrite concentrations (approaching 0.1 M) and result in an artificial decrease of maximal absorbance difference that has previously been assigned to a second low-affinity binding constant (Nicolis et al., *Biochem J* 407:89-99, 2007).

TABLE 2

Nitrite dissociation constants ($K_d$) and bimolecular rate constants (BRC) for reactions of met-Ngb with nitrite in the presence of dithionite

| Neuroglobin protein | $K_d$ ($NO_2^-$) (mM) | BRC of nitrite ferric heme reduction |
|---|---|---|
| WT SS | 6.2 ± 2.1 | 0.0005 ± 0.0005 |
| WT SH | 12.6 ± 3.3 | 0.0002 ± 0.0005 |
| C55A | 30.1 ± 4.5 | 0.0002 ± 0.0005 |
| H64L | 0.17 ± 0.08 | 0.032 ± 0.002 |

These experiments indicate that the redox state of cysteines C46 and C55 regulates both the five-to-six coordinate equilibrium and the rate of nitrite conversion to NO. Intriguingly, an analogous effect is observed with hemoglobin, in which oxidation of the cysteine 93 speeds up the rate of nitrite reduction to NO, and reduction slows the rate (Crawford et al., *Blood* 107:566-574, 2006). This effect has been attributed to the effect of thiol oxidation on decreasing the heme redox potential.

Figure 3A:
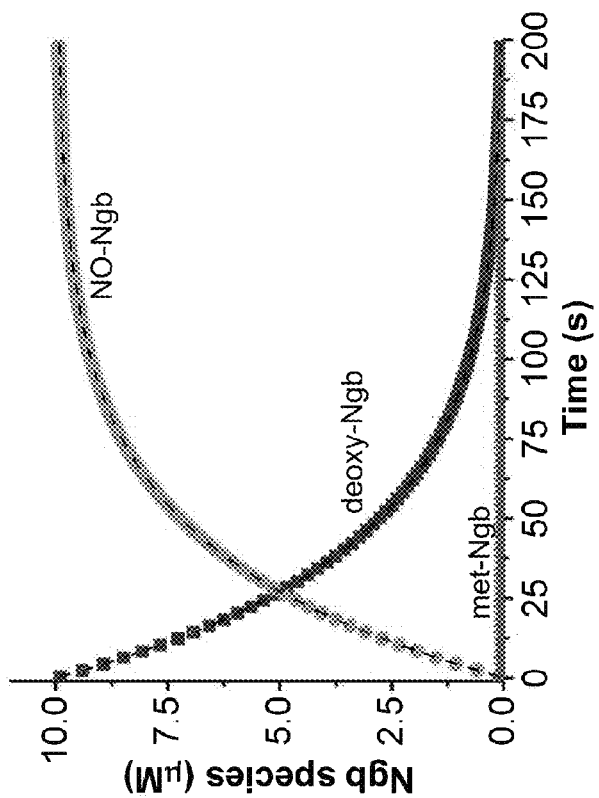
FIG. 3: Kinetics of nitrite reaction with mutant H64L Ngb. (A) and (B) Spectrophotometric analysis of the anaerobic reaction of 10 μM H64L deoxy-Ngb with 100 μM nitrite at pH 7.4, 25° C. and 3 mM dithionite. (C) Plot of $k_{obs}$ versus nitrite concentration (10 μM–1 mM) for H64L Ngb-mediated reduction of nitrite and formation of Ngb Fe(II)NO at pH 7.4 and 25° C. The bimolecular rate constant derived from the linear fit of the data is $259 \pm 8$ M$^{-1}$ s$^{-1}$. (D) Effect of different pH on the nitrite reductase rates. Inset: BRC is linear with the proton concentration. (E) Comparison of representative traces of Ngb wild-type (with reduced and oxidized surface thiols) and mutants H64L and C55A. The absorbance decreases of the Soret peak (425 nm) are plotted as the percentage of the total absorbance change for human Ngb H64L measured at 25° C., pH 7.4.
Figure 3B:
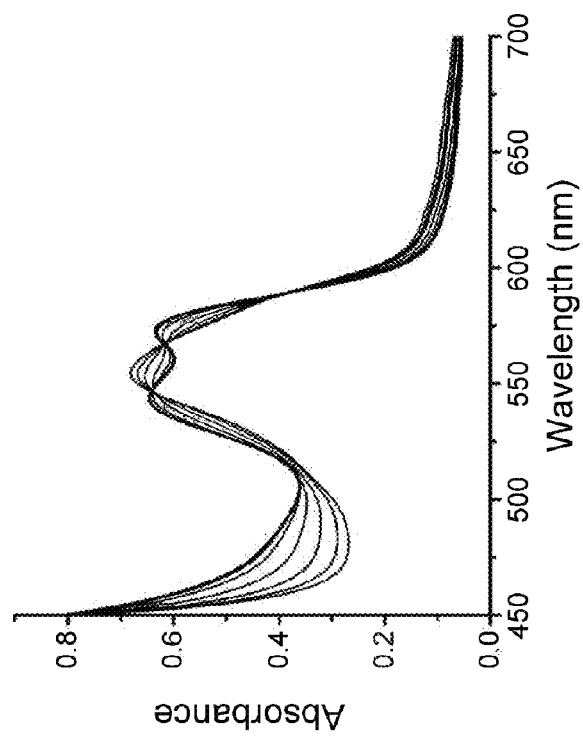
Figure 3D:
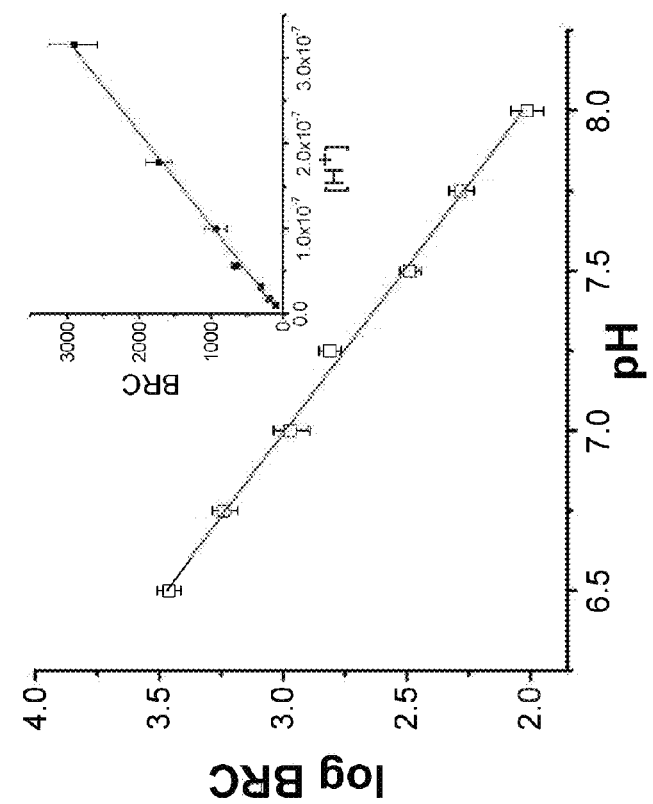
Figure 3C:
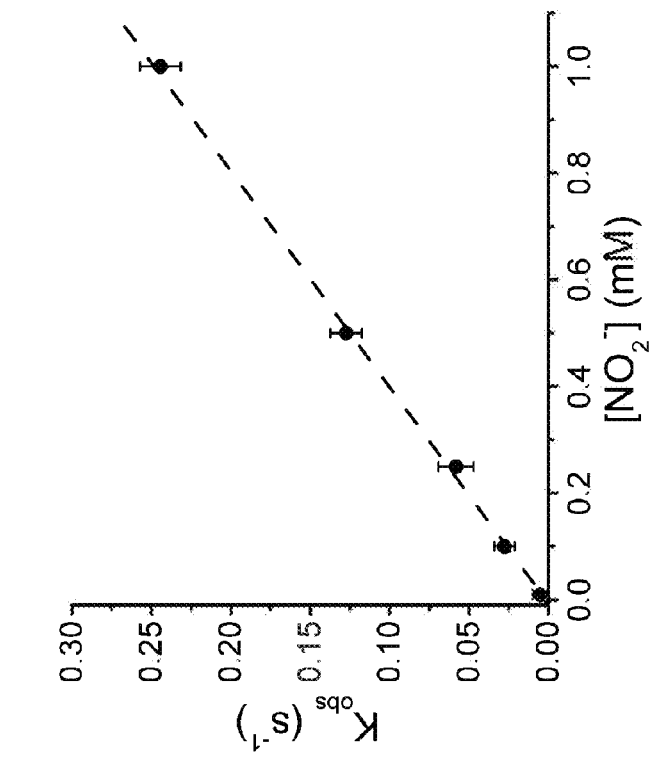
Figure 7B:
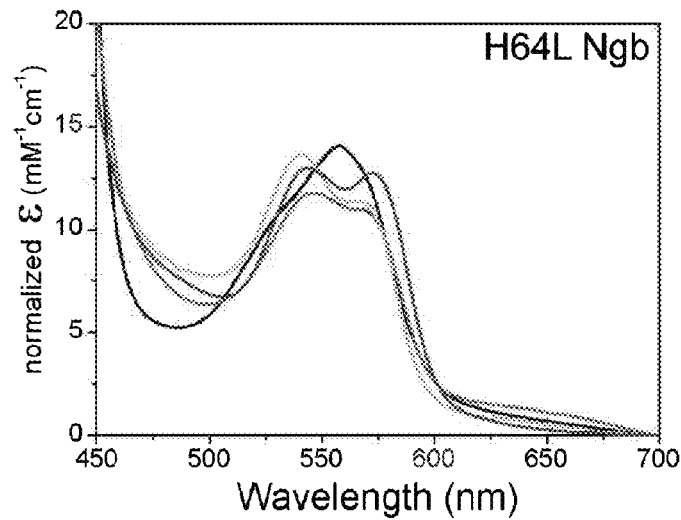
Figure 7C:
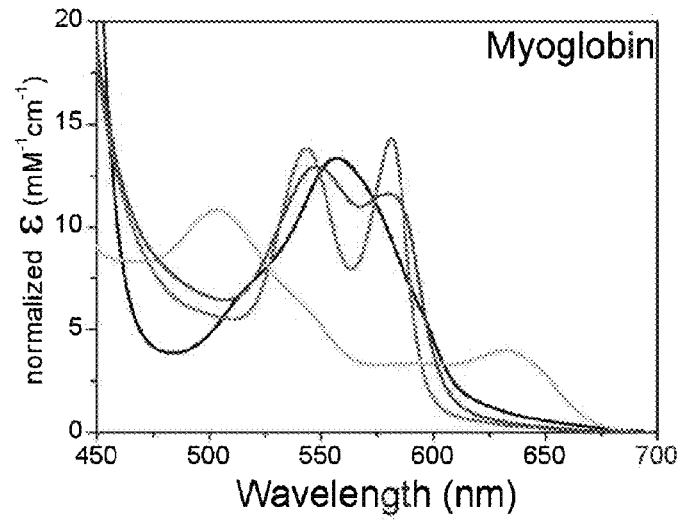

The Rate of Nitrite Reduction is Maximal in the Five-Coordinate State of Neuroglobin To test the hypothesis that a change in the equilibrium between the five- and six-coordinate Ngb sub-populations mediates the control of the nitrite reduction rate, we generated recombinant Ngb with a His64 to Leu substitution (H64L). The absorbance spectra analysis of oxygen bound and deoxygenated ferrous Ngb and ferric Ngb (FIG. 7B) confirmed that the mutant H64L Ngb is "locked" in the five coordinate conformation (Nienhaus et al., *J Biol Chem* 279:22944-22952, 2004) and has very similar spectral characteristics to the classic five coordinate heme proteins hemoglobin and myoglobin (for comparison, FIG. 7C). The reaction of nitrite with deoxygenated H64L Ngb was examined in the presence of excess dithionite similarly to experiments with wild type Ngb, but using only 100 µM nitrite (FIGS. 3A and 3B). Surprisingly, the rate of deoxy-Ngb conversion to nitrosyl-Ngb was extremely fast, and the BRC was approximately 2000-fold higher than the wild type Ngb. Fast mixing stopped-flow spectroscopy was then used to determine the rates of the reaction in the range 10-1000 µM nitrite (FIG. 3C). The observed rate constants increased linearly with increasing nitrite concentrations and the BRC derived from the linear least square fit was 259±8 $M^{-1}$ $s^{-1}$ at 25° C., pH 7.4. Examination of the reaction at different pH values (FIG. 3D) indicates that the reaction requires a proton similar to the reaction with wild type Ngb. Remarkably the rate increases above 2,500 $M^{-1}$ $s^{-1}$ at pH 6.5 and 25° C. This is the fastest reaction of nitrite with a heme-globin ever reported and confirms the hypothesis that the six-to-five coordinate transition at the heme pocket regulates the rate of nitrite reduction to NO.

Figure 3E:
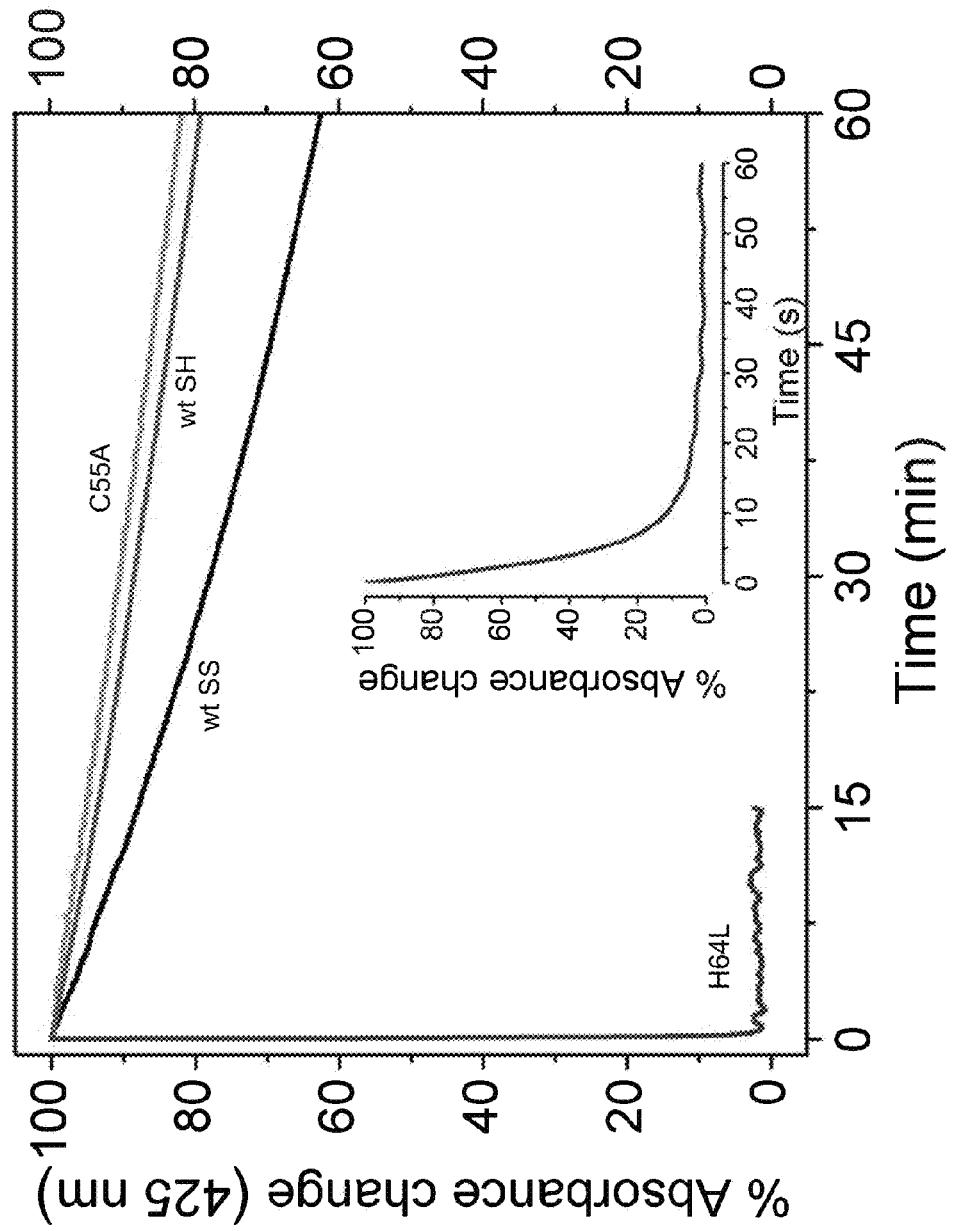

Finally, representative traces (absorbance decreases of the Soret peak at 425 nm) of the reaction of 1 mM nitrite were compared with wild-type Ngb, with or without disulfide bond (SS-Ngb and SH-Ngb respectively), H64L and C55A mutant Ngb in 0.1 M HEPES at pH 7.4. The relative percentage of the total absorbance change occurring in the first 60 minutes of the reaction is shown in FIG. 3E (with H64L-Ngb normalized to 100%, wild-type SS-Ngb was 38%, wild-type SH-Ngb 20%, C55A Ngb 18% respectively). The reaction of five-coordinate H64L Ngb reached the end point in the first minute of the reaction and is expanded in the inset of FIG. 3E.

Figure 4A:
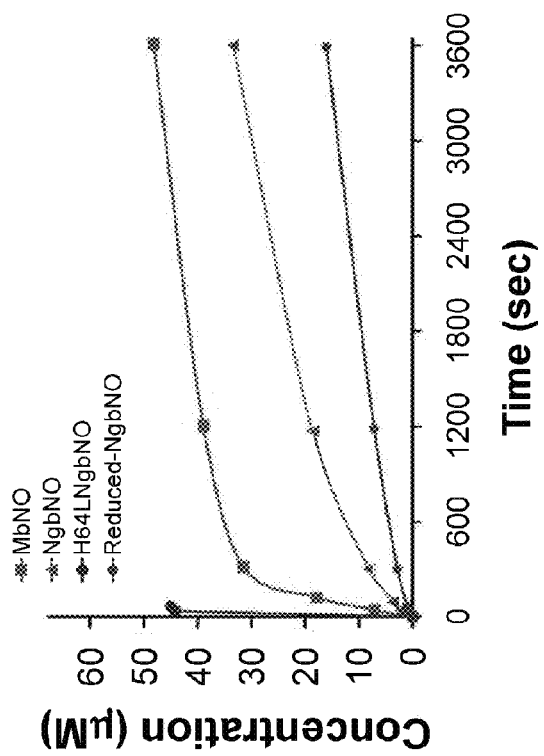
FIG. 4: Electron paramagnetic resonance (EPR) spectroscopy. (A) and (C) EPR spectra showing Fe(II)-NO build-up following addition of indicated amount of nitrite. (B) and (D) The rate of formation of iron-nitrosyl-heme (Fe$^{+2}$—NO) species measured by EPR. The concentrations were determined by performing the double integral calculation and comparing to standard samples.
Figure 4B:
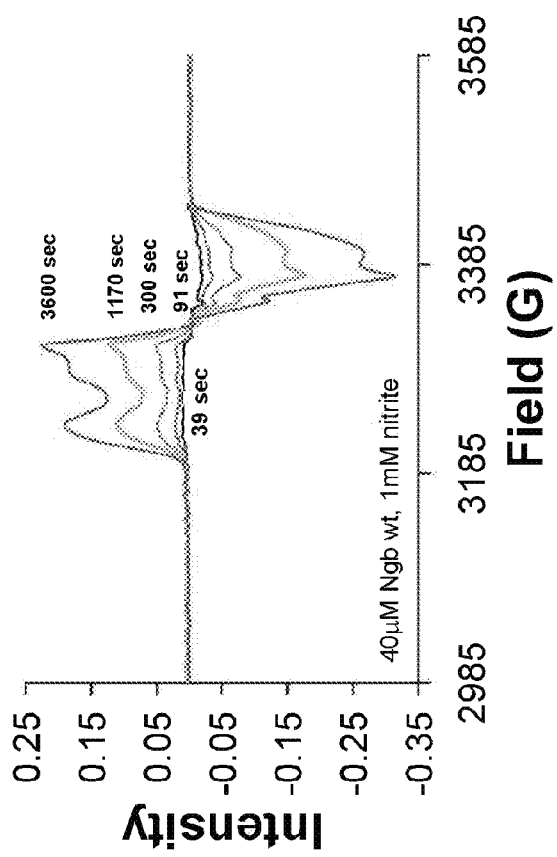
Figures 4C, 4D:
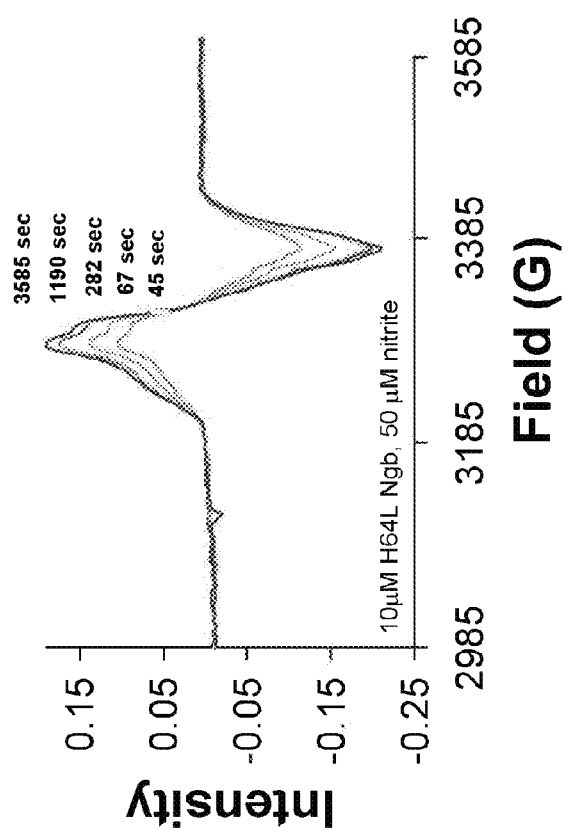

Confirmation of Reaction Kinetics using Electron Paramagnetic Resonance (EPR) Spectrometry EPR spectrometry allows for direct measurement of the paramagnetic NO-heme (iron-nitrosyl) ligand and provides confirmation of NO formation in this reaction. The reaction of 1 mM nitrite with wild-type SS-Ngb, SH-Ngb and mutant H64L Ngb (40±5 µM) was evaluated and compared with the rate of iron-nitrosyl-myoglobin formation (FIGS. 4A and 4B). EPR spectra analysis confirmed that the reduction of the cysteines (stabilizing the six-coordinate heme geometry) slowed the rate of iron-nitrosyl-Ngb formation, while replacement of the distal histidine with leucine (five-coordinate stabilization) dramatically increased the rate of NO formation. In particular, experiments using H64L mutant Ngb and 1 mM nitrite were almost complete in one minute and to allow assessment of the reaction kinetics, lower concentrations of Ngb (10 µM) and nitrite (50 µM) were necessary (FIGS. 4C and 4D). The calculated rates of nitrosyl-Ngb formation are similar to data obtained by absorbance spectrometry.

Nitrite Reduction by Deoxyneuroglobin Generates NO

Figure 5A:
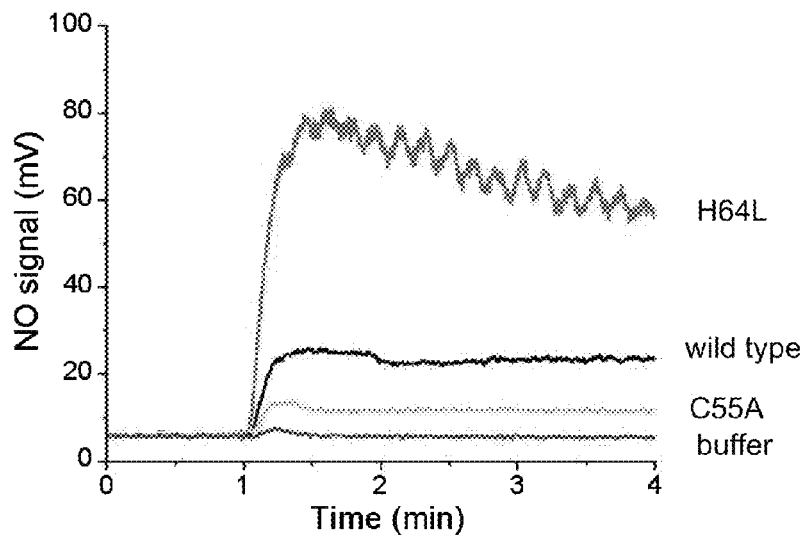
FIG. 5: Nitrite reduction by deoxyneuroglobin generates NO gas. (A) Representative chemiluminescence traces of NO detection in gas phase released during the anaerobic reaction of nitrite with buffer only or 20 μM deoxyNgb wild type, H64L or C55A. (B) Quantification of the rate of NO detected per minute. (C) The nitric oxide signal measured during incubation of 30 μM H64L deoxyNgb and increasing concentrations of nitrite.
Figure 5B:
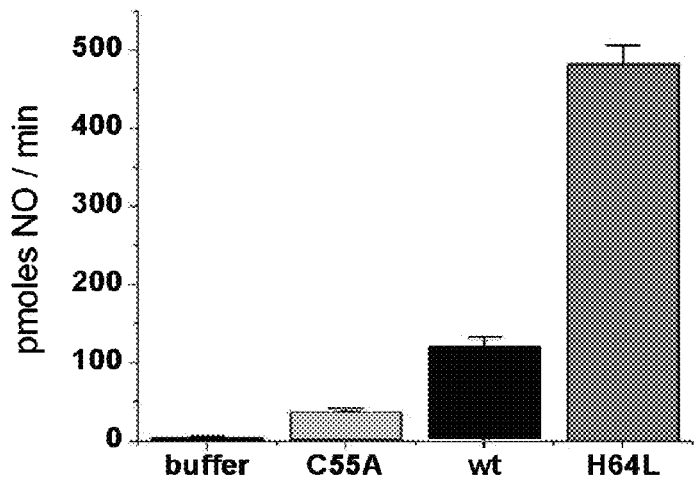
Figure 5C:
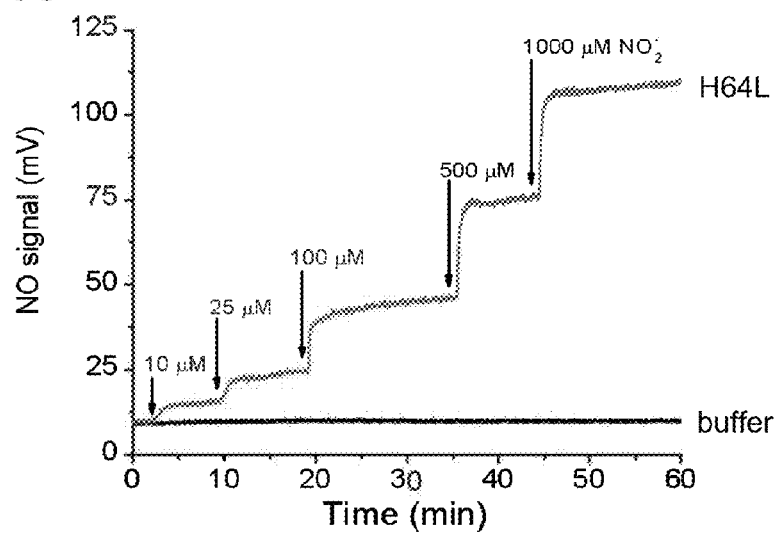

The reaction of nitrite with deoxy-Ngb generates NO and ferric Ngb. Although in in vitro conditions deoxy-Ngb can recapture the NO, it was next explored if free NO gas can escape at measurable rates. Anaerobic Ngb (20 µM) and nitrite (1 mM) were mixed in a vessel purged with helium and carried in-line to a chemiluminescent NO analyzer. In these conditions the anaerobic mixture generated NO in gas phase (FIG. 5A) and the rate of NO formation was again regulated by the cysteines 46-55 disulfide bond and by the heme pocket six-to-five coordination equilibrium. FIG. 5B shows that the rate of NO detected was significantly decreased in reactions with six-coordinate C55A Ngb and increased in reactions with the five coordinate H64L Ngb, consistent with the hypothesis of six-to-five coordinate heme pocket control of nitrite reduction. Finally, when increasing amounts of nitrite (10, 25, 100, 500, 1000 µM final concentrations) were reacated with mutant H64L Ngb (30 µM), the fastest nitrite reductase, a readily proportional NO generation response was observed (FIG. 5C).

Nitrite Reduction by Deoxyneuroglobin Mediates Intracellular NO Signaling

Ngb is expressed in metabolically active cells and organs (neurons, endocrine organs, retina, etc.) and has been hypothesized to interact with mitochondria and mediate cytoprotective responses to ischemic stress (Liu et al., *J Neurosci Res* 87:164-170, 2009). It was therefore hypothesized that the nitrite reductase activity of Ngb may regulate two canonical intracellular signaling pathways: 1) the hypoxic inhibition of cellular respiration by NO binding to cytochrome c oxidase, and 2) the NO-dependent activation of soluble guanylate cyclase to increase the intracellular concentrations of cGMP. NO binding to cytochrome c oxidase has been shown to reversibly inhibit electron transport at low oxygen tensions, in a process thought to contribute physiologically to hypoxic vasodilation and to the extension of oxygen diffusion gradients (Mason et al., *Proc Natl Acad Sci USA* 103:708-713, 2006; Brunori et al., *Biochim Biophys Acta* 1655:365-371, 2004).

Figure 6B:
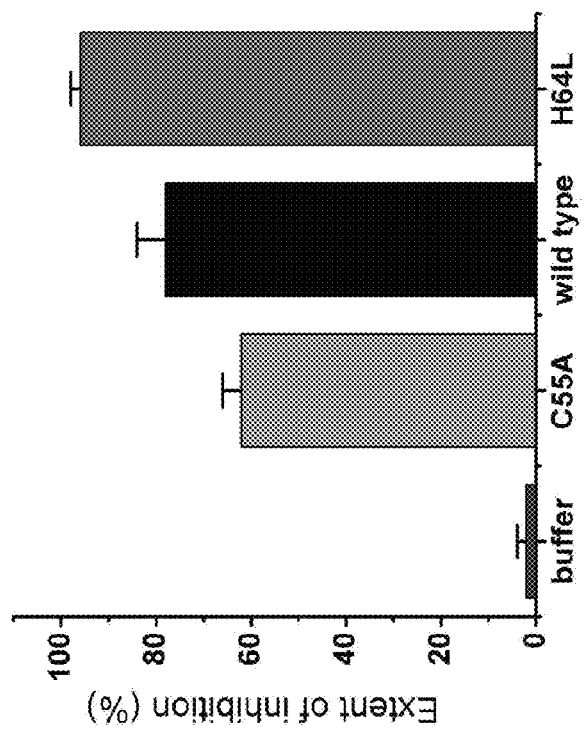
FIG. 6: Deoxyneuroglobin nitrite reduction mediates intracellular NO signaling. (A) Traces of oxygen consumption by isolated mitochondria showing nitrite dependent inhibition of respiration; the early rise in oxygen tension indicates NO-dependent inhibition of cellular respiration which is maximal for cyanide. (B) Comparison of percentage of extent of inhibition (cyanide defined as 100% inhibition) as measured in (A) for isolated mitochondria. (C) Quantification of expression of GFP only, wild type Ngb and H64L mutant Ngb in lentivirus transfected and cloned SHSY5Y cells by Western blot of 4-15% SDS-polyacrylamide gradient gel. (D) Mean extent of hypoxic inhibition of cellular respiration by incubation of SHSY5Y cells expressing GFP, wild type Ngb or H64L Ngb with 20 μM nitrite (*$P<0.01$, **$P<0.05$, compared with control). (E) Intracellular NO signaling mediated by deoxyneuroglobin nitrite reduction determined as cGMP formation in SHSY5Y neuronal cells (*$P<0.01$).
Figure 6A:
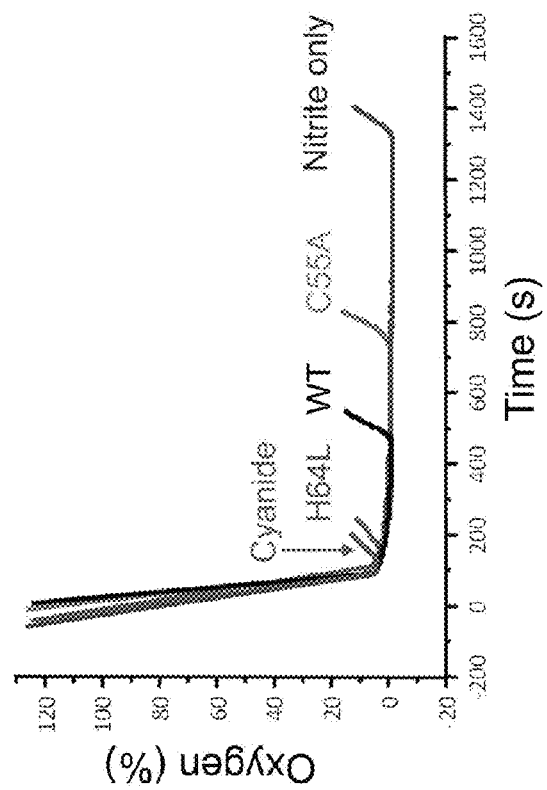
Figure 6D:
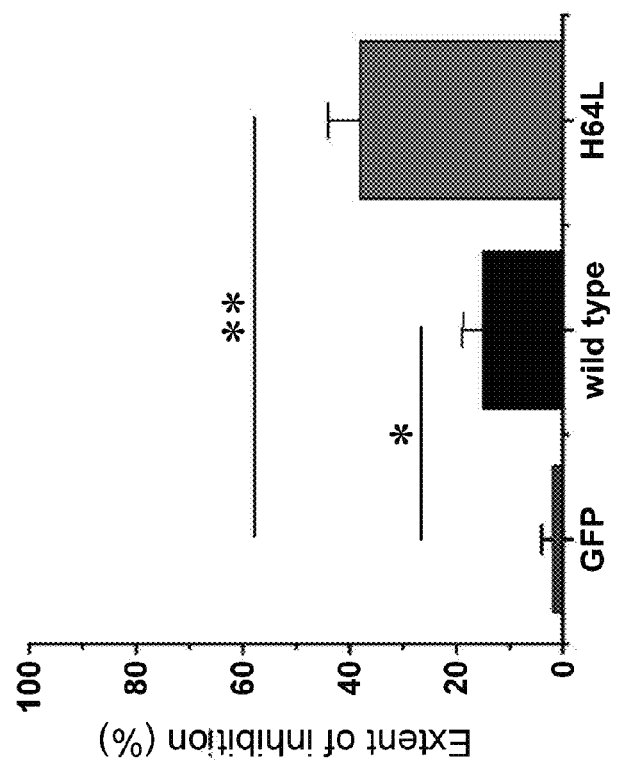
Figure 6C:
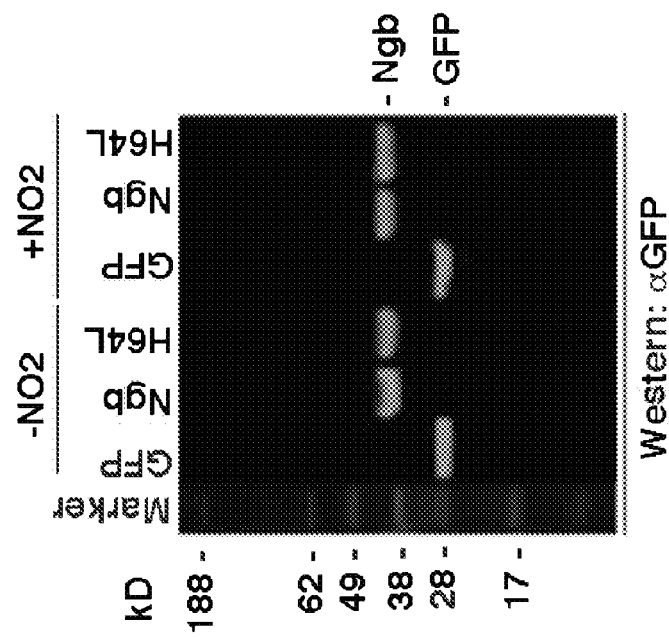

To test whether Ngb generated NO inhibits mitochondrial respiration during hypoxia, isolated rat liver mitochondria were placed in a sealed, stirred respirometer and substrates were added to stimulate respiration as previously described (Shiva et al., *Circ Res* 100:654-661, 2007). Mitochondria were allowed to respire until the ambient oxygen tension dropped below detection level. At this point, the respirometer is opened to air oxygen and cyanide is added to evaluate the time to complete inhibition of respiration, as determined by the increase in oxygen tensions measured with a Clark electrode (FIG. 6A). The extent of mitochondrial inhibition for all experiments was then compared to the effect of cyanide. No significant inhibition of respiration was detected when nitrite (20 µM) or purified wild type Ngb (5 µM) were incubated alone with respiring mitochondria. However, when the same concentrations of nitrite and protein reacted together, 78±6% inhibition of respiration was observed. The extent of inhibition was increased significantly by the H64L mutant Ngb (96±2% inhibition) and decreased by the C55A mutant Ngb (62±4% inhibition) (FIG. 6B). To evaluate this in cells, the cells of the neuronal cell line SHSY5Y were stably transfected using a lentivirus vector with GFP-tagged wild type and H64L mutant Ngb (FIG. 6C) and were used to perform similar experiments. One million intact SHSY5Y cells were suspended in the respirometer and maximal respiration rate was stimulated by addition of the uncoupler FCCP. Then nitrite was added to cells transfected with GFP only (negative control) and cells expressing wild type Ngb or the H64L mutant Ngb. In FIG. 6D, the extent of respiration inhibition was compared to the cyanide effect (complete inhibition): cells with GFP only exhibited no significant inhibition but about 15% and 40% inhibition, respectively, was observed for wild type and H64L Ngb.

Figure 6E:
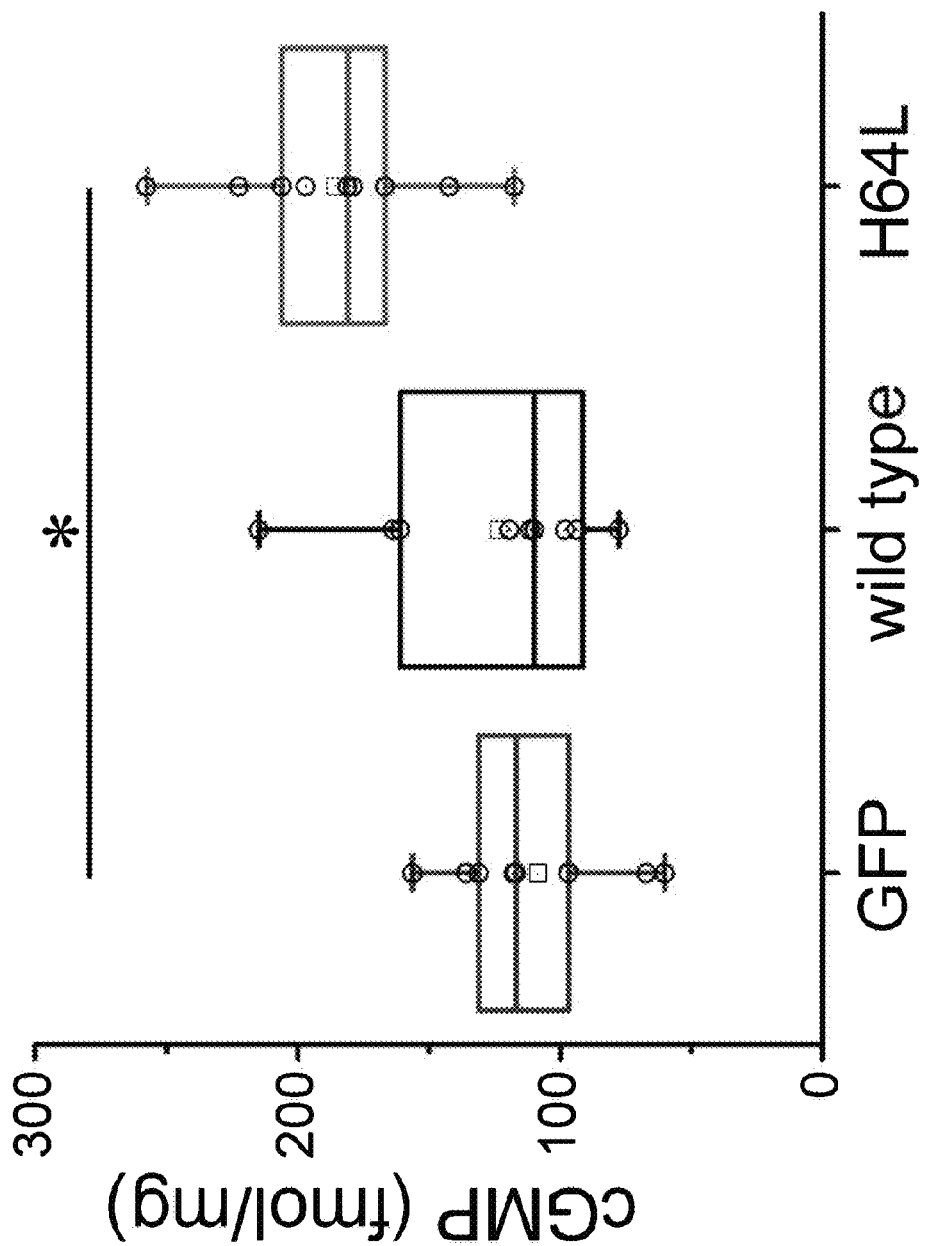

Finally, the effect of Ngb in the activation of sGC during hypoxic conditions was explored. Under basal conditions, SHSY5Y cells expressed neuronal NOS, which generates NO and nitrite under normoxic conditions, for 4 days without added exogenous nitrite then were exposed for 6 hours to hypoxic conditions (1% oxygen). It was found that cGMP levels were significantly increased in cells expressing the five-coordinate H64L mutant neuroglobin (FIG. 6E). Altogether these data demonstrate an interaction between nitrite and deoxygenated neuroglobin that generates bioavailable NO. This can bind to cytochrome c oxidase to inhibit hypoxic mitochondrial respiration and can activate sGC to promote cGMP-dependent intracellular signaling. The extent of mitochondrial inhibition and sGC activation is dependent on the heme coordination structure of neuroglobin and intrinsic nitrite reductase activity.

CONCLUSIONS

The molecular examination of key heme pocket and surface thiol amino acids, using site directed mutagenesis, provides a novel understanding of neuroglobin functionality as an enzyme with a redox regulated six-to-five coordinate iron heme transition that directs nitrite in the heme pocket for controlled electron and proton transfer reactions to form NO. The results presented herein support the provocative hypothesis that the cellular six-coordinate heme globins, neuroglobin, cytoglobin, *Drosophila melanogaster* hemoglobin, and plant hemoglobins may subserve a function as primordial allosterically redox regulated NO synthases. The identification of other allosteric regulators of the six-to-five coordination of the neuroglobin heme pocket may reveal new intracellular mechanisms for controlling NO signaling via nitrite reduction.

Example 3

Administration of Stable Five-Coordinate Neuroglobin to a Human Subject

This example describes that five-coordinate neuroglobin can be used as a blood substitute for treating oxygen deficiency or replacing lost blood in a human subject.

Patient Selection

In one embodiment, the human subject is a human diagnosed with hypoxia, hypoxemia, ischemia, anoxia or another disease for which treatment includes increasing blood oxygenation by administration of a blood substitute, and wherein the human subject is, has been, or will be treated with transfusion of whole blood or a blood substitute. In another embodiment, the human subject is afflicted or is predisposed to being afflicted with a disease or condition treatable by transfusion of whole blood or a blood substitute, for example, anemia, bleeding disorders, burns, coagulopathy, ectopic pregnancy, favism, gastrointestinal bleeding, hemolytic uremic syndrome, hemophilia, microcytosis, ulcer, hemorrhage, rhabdomyolysis, hemorrhagic shock, sickle cell anemia, spherocytosis, thalassemia, or yellow fever. In a further embodiment, the human subject is undergoing, or has undergone, a surgical procedure wherein a clinically dangerous amount of blood has been lost, or wherein a clinically dangerous amount of blood may be lost. In such embodiments, the human subject may develop shock immediately after blood loss occurs, shortly after blood loss occurs, or a longer period of time after blood loss occurs. In some embodiments, the human subject may need to be resuscitated.

In most embodiments, the human subject is under the care of a physician. The physician can identify the presence of a disease or condition treatable by transfusion of whole blood or a blood substitute in the subject according to any methods known to one skilled in the art. A representative method of treatment for such diseases is by administration of stable five-coordinate neuroglobin. The physician can also assess the severity of blood loss in a human subject according to methods known to one skilled in the art, and determine the necessity of blood replacement. A representative method for blood replacement in such subjects is by administration of five-coordinate neuroglobin. In some cases, the patient is further administered a second blood substitute or is administered whole blood or a component of blood.

Administration of Five-Coordinate Neuroglobin Blood Substitute to a Human Subject A therapeutically effective amount of stable five-coordinate neuroglobin (such as H64L human neuroglobin; SEQ ID NO: 9) is administered to the human subject. The five-coordinate neuroglobin blood substitute is administered according to any method known to one skilled in the art. For example, in some embodiments the blood substitute is administered intravenously. In other embodiments, the blood substitute is administered intraarterially. In further embodiments, the blood substitute is administered according to any technique appropriate for transfusion of whole blood.

Patient Recovery and Outcome Assessment

The physician can then assess the therapeutic efficacy of the five-coordinate neuroglobin blood substitute in increasing blood oxygenation in the human subject according to any method known to one skilled in the art, wherein a reduction of symptoms associated with hypoxia in the human subject indicates the effectiveness of the blood substitute in treating pathological blood deoxygenation in the subject.

In some embodiments, the human subject is treated with the five-coordinate neuroglobin blood substitute until the human subject exhibits relief from hypoxia, for example a lessening of one or more hypoxic symptoms or a cure, or inhibition of the development (for instance, prevention) of hypoxia. In such embodiments, treatment with the blood substitute can be discontinued at that point, or it can be continued to an endpoint according to the direction of a physician. It is also possible for the blood substitute to be administered to the human subject during the subject's surgical procedure, or following the surgical procedure. A physician uses methods known to one skilled in the art to assess vascular tone and blood oxygenation during the procedure and during the administration of the blood substitute. Blood substitute is administered according to a regime designed to restore and/or maintain a desirable vascular tone and level of blood oxygenation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of replacing blood in a subject, comprising administering to the subject a therapeutically effective amount of neuroglobin with a stable five-coordinate geometry, wherein the amino acid sequence of the stable five-coordinate neuroglobin is at least 95% identical to SEQ ID NO: 9 and comprises a leucine at amino acid residue 64, thereby replacing blood in the subject.

2. The method of claim 1, wherein the subject has or is at risk of developing a disease, disorder or injury associated with a deficiency in red blood cells and/or hemoglobin, or associated with a reduction in oxygen delivery to tissues.

3. The method of claim 2, wherein the disease, disorder or injury comprises a bleeding disorder, a bleeding episode, anemia, shock, ischemia, hypoxia, anoxia, hypoxaemia, a burn, an ulcer, ectopic pregnancy, microcystosis, rhabdomyolysis, hemoglobinopathy, spherocytosis, hemolytic uremic syndrome, thalassemia, disseminating intravascular coagulation, stroke or yellow fever.

4. The method of claim 3, wherein the bleeding episode results from anticoagulant overdose, aneurysm, blood vessel rupture, surgery, traumatic injury, gastrointestinal bleeding, pregnancy, hemorrhage or infection.

5. The method of claim 3, wherein the bleeding disorder comprises hemophilia A, hemophilia B, hemophilia C, Factor VII deficiency, Factor XIII deficiency, a platelet disorder, a coagulopathy, favism, thrombocytopenia, vitamin K deficiency or von Willebrand's disease.

6. The method of claim 3, wherein the anemia comprises microcytic anemia, iron deficiency anemia, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle-cell anemia, warm autoimmune hemolytic anemia or cold agglutinin hemolytic anemia.

7. The method of claim 3, wherein shock comprises septic shock, hemorrhagic shock or hypovolemic shock.

8. The method of claim 1, wherein the subject suffers from or is at risk of suffering from myocardial infarction, stroke, ischemia-reperfusion injury, pulmonary hypertension or vasospasm.

9. The method of claim 1, wherein the stable five-coordinate neuroglobin is human neuroglobin.

10. The method of claim 9, wherein the human neuroglobin is recombinant human neuroglobin.

11. The method claim 1, wherein the amino acid sequence of the stable five-coordinate neuroglobin is at least 99% identical to SEQ ID NO: 9 and comprises a leucine at amino acid residue 64.

12. The method of claim 1, wherein the amino acid sequence of the stable five-coordinate neuroglobin comprises SEQ ID NO: 9.

13. The method of claim 1, wherein the amino acid sequence of the stable five-coordinate neuroglobin consists of SEQ ID NO: 9.

14. The method of claim 1, wherein the stable five-coordinate neuroglobin is administered to the subject intravenously.

15. The method of claim 1, further comprising administering to the subject a second blood replacement product, a blood product or whole blood.

16. The method of claim 15, wherein the second blood replacement product comprises a hemoglobin-based oxygen carrier, artificial red blood cells or an oxygen releasing compound.

17. The method of claim 15, wherein the blood product comprises packed red blood cells, plasma or serum.

18. The method of claim 1, wherein the subject is a human.

19. The method of claim 1, wherein the subject is a non-human animal.

* * * * *

UNITED STATES PATENT AND TRADEMARK OFFICE
CERTIFICATE OF CORRECTION

PATENT NO. : 9,114,109 B2
APPLICATION NO. : 12/817085
DATED : August 25, 2015
INVENTOR(S) : Gladwin et al.

It is certified that error appears in the above-identified patent and that said Letters Patent is hereby corrected as shown below:

In the Specification

At Column 1, Lines 14-16, "This invention was made with government support grant number HL058091 awarded by the National Institutes of Health. The government has certain rights in the invention" should read –This invention was made with government support under HL058091 awarded by the National Institutes of Health. The government has certain rights in the invention–

Signed and Sealed this
Ninth Day of May, 2023

Katherine Kelly Vidal
*Director of the United States Patent and Trademark Office*